United States Patent
Giri et al.

(10) Patent No.: US 9,533,974 B2
(45) Date of Patent: Jan. 3, 2017

(54) ULTRA-SENSITIVE CHEMILUMINESCENT SUBSTRATES FOR ENZYMES AND THEIR CONJUGATES

(71) Applicant: Michigan Diagnostics, LLC, Royal Oak, MI (US)

(72) Inventors: Brij Pal Giri, Shelby Township, MI (US); Dinesh J. Dagli, Troy, MI (US); Pritam Singh, Shelby Township, MI (US)

(73) Assignee: Michigan Diagnostics, LLC, Royal Oak, MI (US)

( * ) Notice: Subject to any disclaimer, the term of this patent is extended or adjusted under 35 U.S.C. 154(b) by 0 days.

(21) Appl. No.: 14/459,494

(22) Filed: Aug. 14, 2014

(65) Prior Publication Data

US 2015/0031889 A1    Jan. 29, 2015

Related U.S. Application Data

(62) Division of application No. 12/861,453, filed on Aug. 23, 2010, now Pat. No. 8,822,233, which is a division of application No. 11/578,601, filed as application No. PCT/US2005/012680 on Apr. 14, 2005, now Pat. No. 7,781,229.

(60) Provisional application No. 60/562,886, filed on Apr. 14, 2004.

(51) Int. Cl.
| | |
|---|---|
| *G01N 33/533* | (2006.01) |
| *C07D 405/12* | (2006.01) |
| *C09B 15/00* | (2006.01) |
| *C12Q 1/00* | (2006.01) |
| *G01N 33/531* | (2006.01) |
| *G01N 21/76* | (2006.01) |
| *C07H 15/24* | (2006.01) |
| *C07H 15/26* | (2006.01) |

(52) U.S. Cl.
CPC ............ *C07D 405/12* (2013.01); *C07H 15/24* (2013.01); *C07H 15/26* (2013.01); *C09B 15/00* (2013.01); *C12Q 1/00* (2013.01); *G01N 21/76* (2013.01); *G01N 33/531* (2013.01); *G01N 33/533* (2013.01); *Y10S 436/80* (2013.01); *Y10T 436/142222* (2015.01); *Y10T 436/143333* (2015.01); *Y10T 436/20* (2015.01)

(58) Field of Classification Search
CPC .. G01N 33/534; G01N 33/533; G01N 33/531; G01N 21/76; C07D 219/00; C07D 405/12; C09B 15/00; C12Q 1/00; C07H 15/24; Y10S 436/80; Y10T 436/20; Y10T 436/143333; Y10T 436/142222
See application file for complete search history.

(56) References Cited

U.S. PATENT DOCUMENTS

| | | | | |
|---|---|---|---|---|
| 5,032,381 | A * | 7/1991 | Bronstein et al. | 435/4 |
| 5,225,584 | A * | 7/1993 | Brooks et al. | 558/189 |
| 6,461,876 | B1 * | 10/2002 | Giri | 436/546 |
| 2005/0026151 | A1 * | 2/2005 | Voyta et al. | 435/6 |

* cited by examiner

*Primary Examiner* — Shafiqul Haq
(74) *Attorney, Agent, or Firm* — The Weintraub Group, P.L.C.

(57) ABSTRACT

New chemiluminescent compounds, stable in aqueous buffers, for use in biological assaying include acridane-based compounds and 1,2-dioxetanes. Among the new acridane-based compounds are water-soluble acridanes, enhancer coupled acridanes, bis and tris-acridanes as well as acridane-1,2-dioxetanes. Among the new 1,2-dioxetanes are electron deficient group-containing dioxetanes and tethered bis-1,2-dioxetanes. The 1,2-dioxetanes are useful as substrates for various enzymes. The acridanes can be admixed with an oxidizing agent, an aqueous buffer and, optionally, a stabilizer to form a substrate or reagent formulation useful for assaying, inter alia, HRP.

1 Claim, No Drawings

ULTRA-SENSITIVE CHEMILUMINESCENT SUBSTRATES FOR ENZYMES AND THEIR CONJUGATES

CROSS REFERENCE TO RELATED APPLICATION

This application is a divisional application of co-pending U.S. application Ser. No. 11/578,601, which was the National Stage of International Application No. PCT/US05/12680, filed Apr. 14, 2005, which claims the benefit of U.S. Provisional Application No. 60/562,886, filed Apr. 14, 2004, the entire disclosure of which, including all drawings, is hereby incorporated by reference.

BACKGROUND OF THE INVENTION

1. Field of the Invention

This invention relates to a new series of chemiluminescent compounds and their use in the detection of different enzymes such as horseradish peroxidase, alkaline phosphatase, β-galactosidase, β-glucosidase, β-glucuronidase, esterase, sulfatase and the like. The present invention also relates to the synthesis of the new chemiluminescent organic compounds and their use in the detection of different enzymes or their conjugates in aqueous buffers. The present invention further relates to the use of these new chemiluminescent organic compounds for the detection and quantifying of various biological molecules through chemiluminescence as well as detecting DNA or RNA fragments in DNA or RNA sequencing applications and methods of use therefore.

2. Description of Related Arts

Enzyme conjugates are used in enzyme-linked immunosorbent assays, blotting techniques, in-situ hybridization, cytometric and histometric assays. Most frequently horseradish peroxidase, alkaline phosphatase, β-galactosidase, β-glucosidase, β-glucuronidase, arylesterase and sulfatase enzymes are used because of their high turnover rate, stability, and ease of conjugation and relatively low cost. In U.S. Pat. Nos. 6,451,876, 6,602,679 and in pending U.S. Patent Application Ser. Nos. 60/306,041, 60/178,626 and 60/212,883, the disclosures of which are incorporated by reference, there is provided a detailed history of the evolution of chemiluminescence compounds and their uses, which for the sake of brevity need not be totally repeated herein.

Peroxidase enzyme is widely distributed in higher plants and in especially high concentrations in fig sap and horseradish. It is also found in some animal tissues and in microorganisms. Because of its wide availability, horseradish peroxidase (HRP) is widely used in labeling haptens, antibodies, protein A/G, avidin, streptavidin labels and DNA for enzyme immunoassays, immunocytochemistry, immunoblot and DNA detection. Horseradish peroxidase has a molecular weight of 40200 and contains one ferriprotoporphyrin III (protohemin). In protohemin, four of the six coordination bonds of iron interact with the pyrrole ring nitrogens. The other two coordination bonds are occupied by water molecules or hydroxyl anions, depending on the pH. In peroxidase, one of the two remaining coordination bonds is coordinated to a carboxyl group of the protein while the other is coordinated to an amino group or to a water molecule. The structure of ferriprotoporphyrin can be shown as:

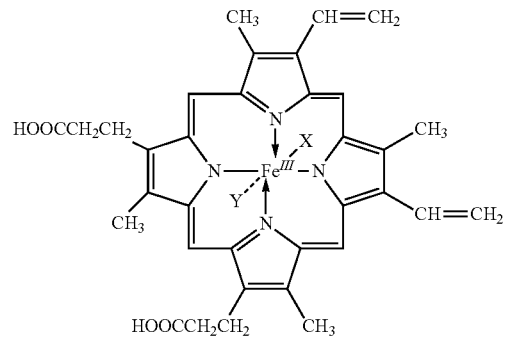

(1)

Peroxidase-based chemiluminescent assays, while demonstrating improved detection sensitivity, suffer from the lack of reproducibility such that the obtained data is not always reliable.

Acridanes have been used as substrates for horseradish peroxidase such as described in U.S. Pat. Nos. 5,523,212; 5,670,644; 5,593,845; 5,723,295 and 5,750,698. These reagents, as a two component system can be stored at lower temperature, but after mixing are not stable. However, stabilized formulations of acridanes use for an extended period of time have been reported in U.S. Pat. No. 6,602,679.

Dioxetanes and, especially, 1,2-dioxetanes are eminently useful to detect the presence, as well as the absence, of certain enzymes in fluids such as blood and the like because of their chemiluminescence. Thus, 1,2-dioxetanes are eminently useful in doing medical assays.

Enzymatic triggerable 1,2-dioxetanes such as those described by A. P. Schaap, R. S. Handley and B. P. Giri. *Tetrahedron Lett.*, 935 (1987); A. P. Schaap, T. S. Chen, R. S. Handley, R. DeSilva, and B. P. Giri, *Tetrahedron Lett.*, 1159 (1987) as well as in U.S. Pat. No. 5,707,550 are superior in immunoassays and other related applications compared to peroxidase substrates such as luminol and others. Stabilized 1,2-dioxetane substrates provide high signal, low background, wide dynamic range, rapid results and excellent reproducibility. These 1,2-dioxetanes provide substrates which are highly sensitive and can detect an enzyme concentration up to $10^{-21}$M ($6 \times 10^2$ molecules of alkaline phosphatase) in solution as well as on a membrane. The comparative detection limit of alkaline phosphatase using fluorescence, time-resolved fluorescence and colorimetric techniques is $10^{-19}$ M ($6 \times 10^4$ molecules), $3 \times 10^{-19}$ M ($1.8 \times 10^5$ molecules) and $5 \times 10^{-17}$ M ($3 \times 10^8$, molecules), respectively.

Other useful 1,2-dioxetanes are those disclosed in the U.S. Pat. No. 6,461,876, the disclosure of which is hereby incorporated by reference.

Alkaline phosphatases (orthophosphoric monoester phosphohydrolase, alkaline optimum) are found primarily in animal tissues and microorganisms. Alkaline phosphatases used in Enzyme Immuno Assays (EIA) are isolated from bovine intestinal mucosa or from *E. coli*. These enzymes have considerable differences in their properties and, ordinarily, can not be assayed under identical conditions. The bacterial enzyme has lower activity than the bovine intestinal enzyme.

Alkaline phosphatases hydrolyze numerous esters, such as those of primary and secondary alcohols, phenols and amines. A major reason for the popularity of alkaline phosphatase for EIA is its absence from higher plants. The enzyme is abundant in animals and human tissues involved in nutrient transport and in developing tissues and secretory organs, but it is not found in significant amounts in muscle, connective tissue or cartilage. Some pathological conditions increase alkaline phosphatase activities in sera. Reporter gene assays are also invaluable in the study of gene regulatory elements.

Reporter genes are those that encode proteins that can be unambiguously assayed once they are incorporated within a living cell. When reporter genes are fused with other genes or with genomic regulatory elements, the resulting DNA constructs can be introduced into the cell of interest, and the reporter gene product (an enzyme) can than be assayed. This technique can be used to identify DNA sequences or regulatory proteins that are required for proper gene expression.

β-D-Galactosidase galactohydrolase or β-galactosidase enzyme has been detected in numerous microorganisms, animals and plants. In some E. coli strains about 5% of the total protein content is β-galactosidase if lactose is the sole source of carbon. Its large molecular size makes it less suitable for Enzyme Immuno Histology (EIH) but is one of the most commonly used enzymes for reporter gene assays. The gene that encodes β-galactosidase (lac Z) is a commonly used reporter gene in molecular biology.

β-Glucosidase enzyme is present in nearly all species. It is reported that people with Gaucher's disease have β-glucosidase gene mutations, which results in abnormal lysosomal storage.

β-Glucuronidase enzyme is present in plant and mammalian cells. The E. coli GUS gene, which encodes β-glucuronidase, is a major marker for detecting transformed plant cells. β-Glucuronidase is a widely used reporter gene in plant genetic research.

Aryl esterase enzyme catalyzes the hydrolysis of lower fatty acid esters such as methyl butyrate. Aryl esterase is used to catalyze the cleavage of an acetate-substituted 1,2-dioxetanes at ambient temperature in 0.1M phosphate buffer.

Aryl sulfatase is used to catalyze the cleavage of a sulfate-substituted 1,2-dioxetanes at ambient temperature in 0.1M tris buffer and 0.5M acetate buffer.

However, there still exists a need for new, better and more suitable enzyme substrates. As describe below, the present invention address is this.

SUMMARY OF THE INVENTION

The present invention provides new, highly sensitive chemiluminescent organic compounds which are useful to produce light in anaqueous buffer.

The present invention provides chemiluminescent substrates for different enzymes and their conjugates used in the detection of antibodies or antigen in biological fluids and for compounds, particularly toxins and contaminants, in the environment and food.

In a full aspect hereof, the present invention provides a new series of acridanes for use in chemiluminescent detection. The new acridanes being include deuterium-based substituted acridanes, water soluble group containing acridanes, enhancer-coupled substituted acridanes, 1,2-dioxetanes-coupled substituted acridanes, bis-acridanes and tris-acridanes.

The deuterium atom or deuterium atom containing substituted acridanes generally correspond to the formula:

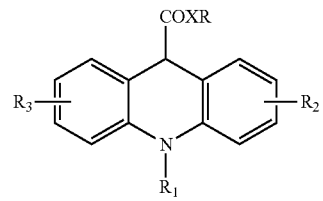

(2)

X is oxygen, nitrogen or sulfur; R is methyl, deuterated methyl, phenyl, deuterated phenyl or substituted phenyl; $R_1$ is alkyl (containing up to six carbon atoms, branched or normal chain) or deuterated alkyl, aryl or deuterated aryl, arylalkyl, alkylaryl, heteroalkyl, alkylalkene, arylalkene, alkylnitrile, alkylalcohol and alkyacid; $R_2$ and $R_3$ may be alkyl or deuterated alkyl, methoxy or deuterated methoxy, Cl, Br or CN; wherein at least one of R, $R_1$, $R_2$, and $R_3$ is a deuterium atom or deuterium atom containing organic group.

The water soluble group containing or water-soluble acridanes can be shown as:

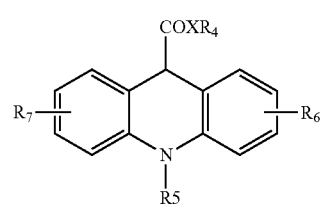

(3)

X is oxygen, nitrogen or sulfur; wherein $R_4$ is an organic group to increase the solubility of substituted acridanes in an aqueous buffer; $R_5$, $R_6$ and $R_7$ are the same as $R_1$, $R_2$ and $R_3$ are in structure (2).

The third class of acridanes provided herein are shown as:

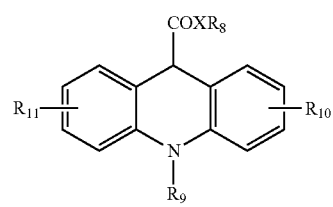

(4)

wherein $R_8$ is a substituent for increasing light output in an aqueous buffer in a chemiluminescent system, $R_9$, $R_{10}$, and $R_{11}$ are organic groups in the acridane ring as $R_1$, $R_2$ and $R_3$ are in structure (2); X is oxygen, nitrogen or sulfur.

The present invention further provides substituted acridanes corresponding to the formula:

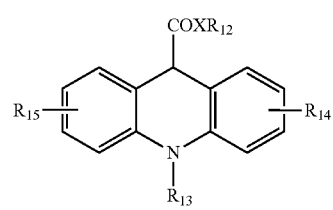

(5)

wherein $R_{12}$ a is substituted 1,2-dioxetane, $R_{13}$, $R_{14}$, and $R_{15}$ are the substitution in acridane ring as $R_1$, $R_2$ and $R_3$ are in structure (2); X is oxygen, nitrogen or sulfur.

The present invention further provide substituted bis or tris-acridanes which are used as horseradish peroxidase enzyme substrates. The general structure of these bis or tris-acridanes can be shown as:

(6)

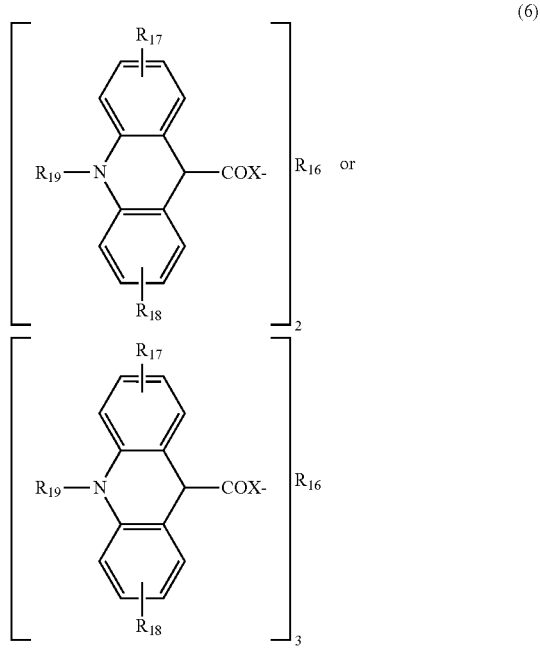

wherein $R_{16}$ is alkyl or substituted alkyl, aryl or substituted aryl, alkylaryl or substituted alkylaryl, and $R_{17}$, $R_{18}$, and $R_{19}$ are substituents in the acridane ring which may include a deuterium atom or deuterium atom containing group; X is oxygen, nitrogen or sulfur, wherein $R_{19}$ may be alkyl or deuterated alkyl, aryl or deuterated aryl, arylalkyl, alkylaryl, heteroalkyl, alkylalkene, arylalkene, alkylnitrile, alkylalcohol and alkyacid; $R_{17}$ and $R_{18}$ correspond to $R_2$ and $R_3$ above.

A second aspect of the present invention provides a first class of new 1,2-dioxetanes.

The new class of new 1,2-dioxetanes correspond to the formula:

(7)

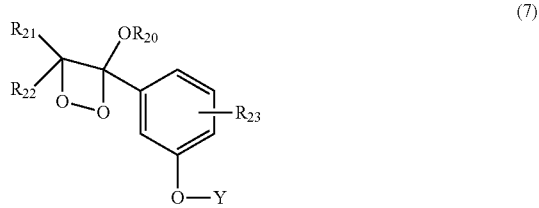

wherein Y is hydrogen, alkyl, acetate, t-butyldimethylsilyl or other protecting group, an enzyme cleaveable group or an antibody cleaveable group, $R_{23}$ is a substitution in the benzene ring such as hydrogen, a deuterium atom, a deuterium atom-containing group, halogen, hydroxy or substituted hydroxy, nitrile, alkyl, alkaryl, aralkyl, amino or substituted amino, nitro, aldehyde, acid, amide, aryl or substituted aryl, $R_{20}$ is an organic group having an isotopic hydrogen (deuterium atom) and is selected from the group consisting of cyclic, linear or branched, halogenated or non-halogenated alkyl, aryl, arylalkyl, alkaylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid, $R_{21}$ and $R_{22}$ (I) form

which is a cyclic, polycyclic or spiro-fused ring containing at least one carbon-carbon double bond or carbon-carbon triple bond in the ring or side chain, with or without heteroatoms, or (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) are each substituted or unsubstituted branched alkyl groups or cycloalkyl groups having 3 to 8 carbon atoms and being substituted in the ring or side chain.

A second class of new 1,2-dioxetanes are tethered bis-1, 2-dioxetanes. These tether bis-1,2-dioxetanes are prepared by the photo-oxidation of tethered bis-alkenes. The bis-1,2-dioxetanes hereof generally correspond to the formula:

I

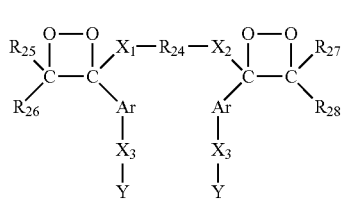

(8)

$X_1$, $X_2$ and $X_3$ are each individually, sulphur or oxygen or nitrogen; $R_{24}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{25}$ and $R_{26}$ (I) form

which is a cyclic, polycyclic or spiro-fused ring containing at least one carbon-carbon double bond or carbon-carbon triple bond in the ring or side chain, with or without heteroatoms, or (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) are each substituted or unsubstituted branched alkyl groups or cycloalkyl groups having 3 to 8 carbon atoms and being substituted in the ring or side chain, Ar is either phenyl, substituted phenyl, naphthyl, substituted naphthyl, anthryl, substituted anthryl with or without a fluorescent group; Y is either hydrogen, alkyl, acetate, t-butyldimethylsilyl, an enzyme cleavable group or an antibody cleavable group; and $R_{24}$ is an organic group having an isotopic hydrogen (deuterium atom) and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{27}$ and $R_{28}$ are the same as $R_{25}$ and $R_2$, wherein individually $R_{24}$, $R_{25}$, $R_{26}$, $R_{27}$, $R_{28}$ and Ar may be a deuterium atom or deuterium atom containing organic group;

or

II (9)

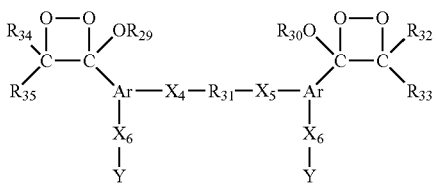

$X_4$, $X_5$ and $X_6$ are each individually sulphur, oxygen or nitrogen; $R_{29}$ and $R_{30}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{32}$ and $R_{33}$ (I) form

which is a cyclic, polycyclic or spiro-fused ring containing at least one carbon-carbon double bond or carbon-carbon triple bond in the ring or side chain, with or without heteroatoms, or (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) are each substituted or unsubstituted branched alkyl groups or cycloalkyl groups having 3 to 8 carbon atoms and being substituted in the ring or side chain, Ar is either phenyl, substituted phenyl, naphthyl, substituted naphthyl, anthryl, substituted anthryl with or without a fluorescent group; Y is either hydrogen, alkyl, acetate, t-butyldimethylsilyl, an enzyme cleavable group, or an antibody cleavable group; and $R_{31}$ is a aryl or alkyl linker arm; $R_{34}$ and $R_{35}$ are as described above for $R_{32}$ and $R_{33}$ or

III (10)

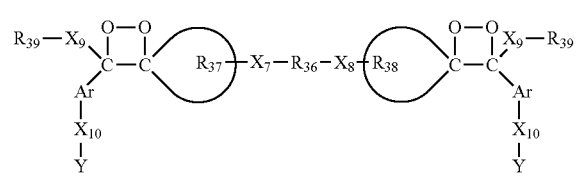

wherein $R_{36}$, $R_{37}$, $R_{38}$, $R_{39}$ and Ar may include a deuterium atom or deuterium atom containing organic group; $X_7$, $X_8$, $X_9$ and $X_{10}$ are each individually sulphur, oxygen or nitrogen, Y is either hydrogen, alkyl, acetate, t-butyldimethylsilyl, an enzyme cleavable group, or an antibody cleavable group; $R_{36}$ is an aryl or alkyl linker arm; $R_{39}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl (etheralkyl)$_2$, alkyl(etheralkyl)$_3$, alkyletherhaloalkyl, alkyl (etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{37}$ (I) form

which is a cyclic, polycyclic or spiro-fused ring containing at least one carbon-carbon double bond or carbon-carbon triple bond in the ring or side chain, with or without heteroatoms, (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) a substituted or unsubstituted branched alkyl groups or cycloalkyl groups having 3 to 8 carbon atoms and being substituted in the ring or side chain; $R_{38}$ is as described above for $R_{37}$, wherein individually $R_{29}$, $R_{30}$, $R_{31}$, $R_{32}$, $R_{33}$, $R_{34}$, $R_{35}$ and Ar may comprise a deuterium atom or deuterium atom containing organic group;

or

IV (11)

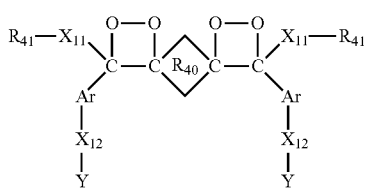

$X_{11}$ and $X_{12}$ are each, individually, sulphur, oxygen or nitrogen, Y is either hydrogen, alkyl, acetate, t-butyldimethylsilyl, an enzyme cleavable group, or an antibody cleavable group; $R_{40}$ (I) forms

which is a cyclic, polycyclic or spiro-fused ring containing at least one carbon-carbon double bond or cabon-carbon triple bond in the ring or side chain, with or without heteroatoms, or (II) forms

which is a cyclic, polycyclic or a spiro-fused ring containing a substituted or unsubstituted fused aromatic ring or a substituted or unsubstituted aromatic ring attached by linker arms, or (III) forms

which is either a cyclic, substituted or unsubstituted polycyclic alkyl group which is spiro-fused to the dioxetane ring or (IV) is a substituted or unsubstituted branched alkyl groups or cycloalkyl groups having 3 to 8 carbon atoms and being substituted in the ring or side chain; $R_{41}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl (etheralkyl)$_2$, alkyl(etheralkyl)$_3$, alkyletherhaloalkyl, alkyl (etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; and Ar either phenyl, substituted phenyl, naphthyl, substituted naphthyl, anthryl, substituted anthryl with or without a fluorescent group, wherein each of $R_{40}$, $R_{41}$, and Ar may include a deuterium atom or deuterium atom containing organic group.

These new ultra-sensitive 1,2-dioxetanes can detect β-glucosidase, β-glucosidase, β-glucuronidase, esterase and sulfatase enzymes at very low level. These chemiluminescent systems are at least 1000 times more sensitive compared to the chromophoric substrates.

The deuterium atom or deuterium atom containing group effects the output of chemiluminescent light produced by the enzymatic decomposition of 1,2-dioxetanes.

For a more complete understanding of the present invention references is made to the following detailed description and accompanying examples.

DESCRIPTION OF THE PREFERRED EMBODIMENTS

In a first aspect hereof and as noted above, the present invention provides new acridane-based chemiluminescent compounds for uses in an aqueous buffer.

These chemiluminescent compounds are used to prepare stabilized substrate in aqueous buffer or reagent formulations for use in assaying HRP enzyme or its conjugates and other molecules from biological sources.

In accordance with the first aspect there is provided deuterium-based substituted acridanes; water-soluble substituted acridanes; enhancer-coupled substituted acridanes; 1,2-dioxetanes-coupled substituted acridanes and bis- and tris-substituted acridanes. These are more particularly discovered herebelow.

Deuterium-Based Substituted Acridanes:

A deuterium atom or deuterium atom-containing group effects the output of chemiluminescent light produced by the enzymatic decomposition of 1,2-dioxetanes. The deuterium atom or deuterium atom containing substituted acridanes hereof generally correspond to the formula:

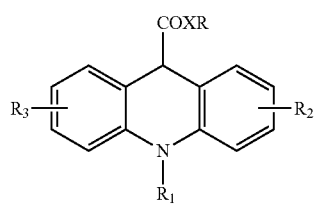

(2)

X is oxygen, nitrogen or sulfur; R is methyl, deuterated methyl, phenyl, deuterated phenyl or substituted phenyl; $R_1$ is alkyl (containing up to six carbon atoms, branched or normal chain) or deuterated alkyl, aryl or deuterated aryl, arylalkyl, alkylaryl, heteroalkyl, alkylalkene, arylalkene, alkylnitrile, alkylalcohol and alkyacid; $R_2$ and $R_3$ may be alkyl or deuterated alkyl, methoxy or deuterated methoxy, Cl, Br or CN; wherein at least one of R, $R_1$, $R_2$, and $R_3$ is a deuterium atom or deuterium atom containing organic group.

Generally, these acridanes are prepared by the reaction of a substituted acridane acid chloride and phenols or deuterated phenols or alcohols or deuterated alcohols in the presence of suitable base such as pyridine or diisopropylethylamine, under a nitrogen or argon blanket at a temperature ranging from about 5° C. o about 35° C. for a period of about 10 minutes to 48 hours.

Typically used acid chlorides are prepared by the reaction of an acridanes carboxylic acid and thionyl chloride.

Water Soluble Substituted Acridanes:

The general structure of these molecules can be shown as:

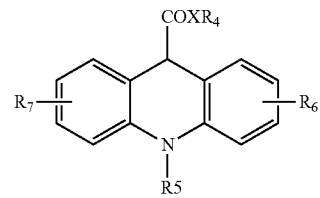

(3)

X is oxygen, nitrogen or sulfur; wherein $R_4$ is an organic group to increase the solubility of substituted acridanes in an aqueous buffer; $R_5$, $R_6$ and $R_7$ are the same as $R_1$, $R_2$ and $R_3$ are in structure (2). Among the useful water solubility increasing groups are p-hydroxycinnamic acid, p-ainocinnamic acid and 4-(4' hydroxyphenoxy)phenol, These acridanes are prepared by the reaction of substituted acridane acid chloride and p-hydroxycinnamic acid or p-aimocinnamic acid or 4-(4' hydroxyphenoxy) phenol in the presence of a suitable base under a nitrogen or argon blanket at the same necessary parameters noted above.

Enhancer Coupled Substituted Acridanes:

The present invention, as noted, provides here the general structure of these substituted acridanes can be shown as:

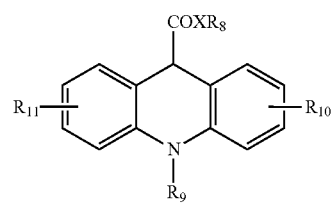

(4)

wherein $R_8$ is a substituent for increasing light output in an aqueous buffer in a chemiluminescent system, $R_9$, $R_{10}$, and $R_{11}$ are organic groups in the acridane ring as $R_1$, $R_2$ and $R_3$ are in structure (2); X is oxygen, nitrogen or sulfur. Among the useful enhancer group which may, also, increase water solubility are p-hydroxycinnamic acid, p-ainocinnamic acid, 4-(4'hydroxyphenoxy)phenol, 6-hydroxybenzothiazole, p-phenylphenol, p-iodophenol.

These acridanes are prepared by the reaction of substituted acridane acid chloride and the enhancer in the presence of a suitable base under a nitrogen or argon blanket at the same necessary parameters noted above.

The enhancer-coupled acridanes will release the enhancer molecule after reacting with HRP-Fe$^V$=O in an aqueous buffer. The reaction sequence can be shown as:

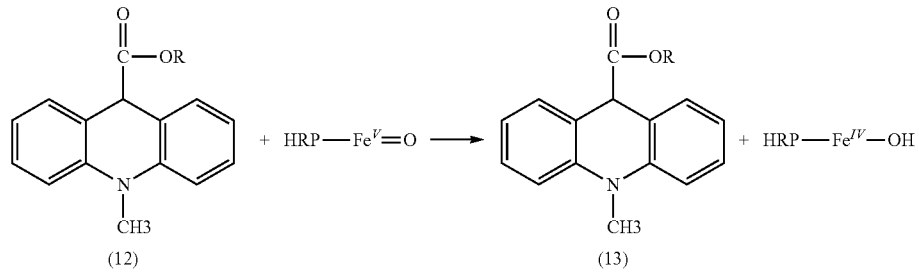

(12)    (13)

H$_2$O$_2$/under basic conditions

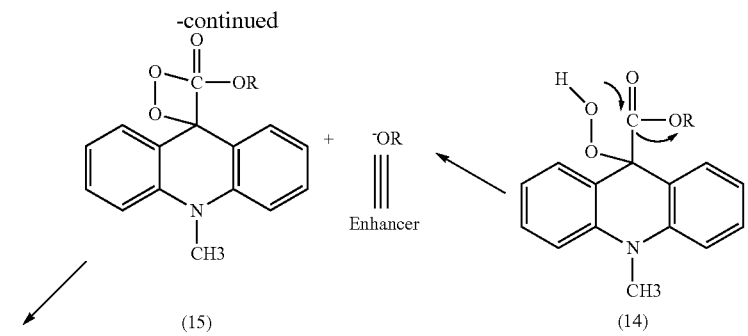

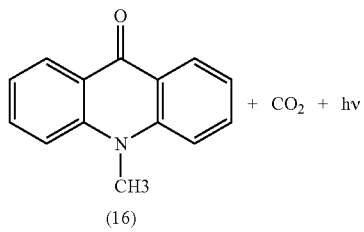

The released enhancer accelerates the reaction of acridane and HRP-Fe$^V$=O for to generate greater chemiluminescence.

1,2-Dioxetanes Coupled Substituted Acridanes

The decomposition of 1,2-dioxetanes by horseradish peroxidase enzyme is not known in the literature. It has been found that these substituted 1,2-dioxetanes hereof can be triggered by horseradish peroxidase enzyme. The general structure can be shown as:

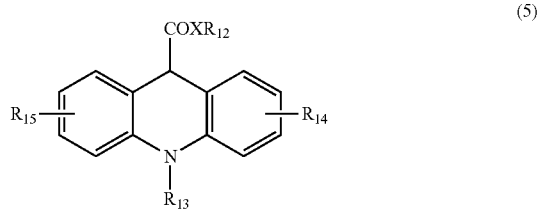

wherein $R_{12}$ a is substituted 1,2-dioxetane, including [(4-methoxy)-4-(3-hydroxyphenyl)]spiro[1,2-dioxetane-3,13'-tricyclo[7.3.1.0$^{2,7}$]tridec-2,7-ene], $R_{13}$, $R_{14}$, and $R_{15}$ are the substitution in acridane ring as $R_1$, $R_2$ and $R_3$ are in structure (2); X is oxygen, nitrogen or sulfur These acridanes are prepared by the reaction of substituted acridanes acid chloride and the stabilized substituted 1,2-dioxetanes in the presence of a suitable base, such as pyridine or diisopropylamine under a nitrogen or argon blanket.

Although not wishing to be biased by any theory, it appears that the most probable mechanism for the decomposition of the present acridanes-1,2-dioxetanes is the formation of a phenoxide ion which, on decomposition, under basic conditions, gives off light, and this can be shown as:

HRP-Fe$^V$=O+EH→HRP-Fe$^{IV}$—OH+E.

HRP-Fe$^{IV}$—OH+EH→HRP-Fe$^{III}$+E+H$_2$O

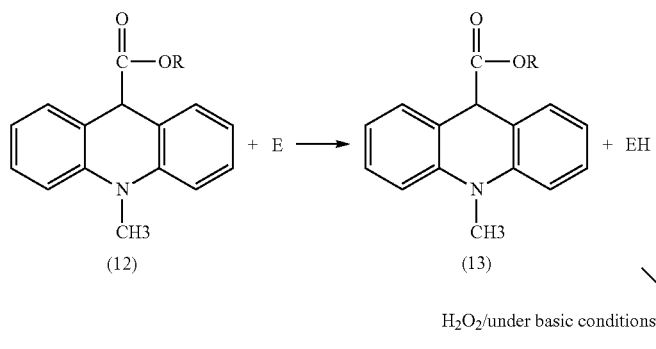

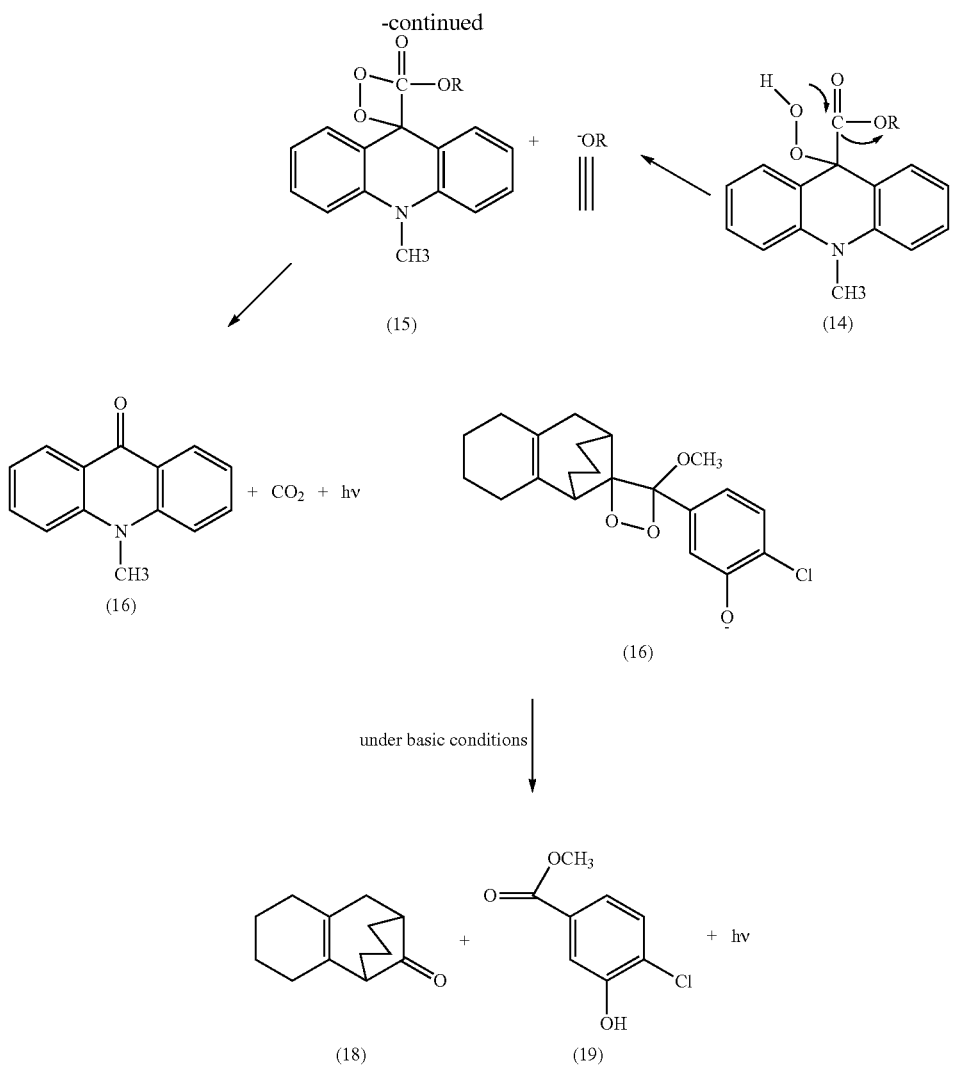

Bis- and tris-acridanes

As noted above, the present invention, also provide bis- and tris-acridanes for use as chemiluminescent compounds. These can be shown as:

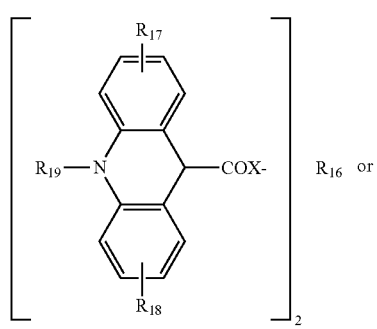

(6)

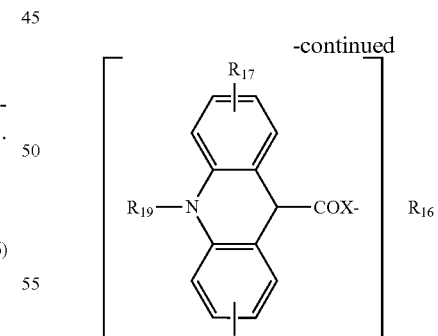

wherein $R_{16}$ is alkyl or substituted alkyl, aryl or substituted aryl, alkylaryl or substituted alkylaryl, and $R_{17}$, $R_{18}$, and $R_{19}$ are substituents in the acridane ring which may include a deuterium atom or deuterium atom containing group; X is oxygen, nitrogen or sulfur, wherein $R_{19}$ may be alkyl or deuterated alkyl, aryl or deuterated aryl, arylalkyl, alkylaryl, heteroalkyl, alkylalkene, arylalkene, alkylnitrile, alkylalcohol and alkyacid; $R_{17}$ and $R_{18}$ correspond to $R_2$ and $R_3$ above.

The present acridanes, as noted, may be used to prepare stabilized chemiluminescent reagents when admixed with an oxidizing agents, a buffer and/or a stabilizing agent.

As noted hereabove and in a second aspect hereof there is provided a new class of 1,2-dioxetanes including electron-deficient group containing dioxetanes and tethered bis-1,2-dioxetanes.

The present invention, also, provide new alkenes for the production of the 1,2-dioxetanes. These 1,2-dioxetanes may be used for the detection of alkaline phosphatase, β-galactosidase, β-glucosidase, β-glucuronidase, esterase, and sulfatase.

Electron Deficient Group Containing 1,2-Dioxetanes;

The electron deficient group containing 1,2-dioxetanes can be represented as:

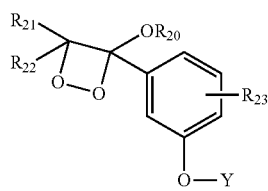

(7)

wherein Y is hydrogen, alkyl, acetate, t-butyldimethylsilyl or other protecting group, an enzyme cleaveable group or an antibody cleaveable group, $R_{23}$ is a substitution in the benzene ring such as hydrogen, a deuterium atom, a deuterium atom-containing group, halogen, hydroxy or substituted hydroxy, nitrile, alkyl, alkaryl, aralkyl, amino or substituted amino, nitro, aldehyde, acid, amide, aryl or substituted aryl, $R_{20}$ is an organic group having an isotopic hydrogen (deuterium atom) and is selected from the group consisting of cyclic, linear or branched, halogenated or non-halogenated alkyl, aryl, arylalkyl, alkaylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid, $R_{21}$ and $R_{22}$ (I) form

which is a cyclic, polycyclic or spiro-fused ring containing at least one carbon-carbon double bond or cabon-carbon triple bond in the ring or side chain, with or without heteroatoms, or (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) are each substituted or unsubstituted branched alkyl groups or cycloalkyl groups having 3 to 8 carbon atoms and being substituted in the ring or side chain.

As described below electron deficient group containing 1,2-dioxetanes hereof are synthesized by the oxidation of a new series of substituted alkenes containing electron deficient or electron withdrawing groups. Ar is a substituted or unsubstituted aromatic ring having an electron withdrawing group or groups such as Cl or CN, $R_{20}$ $R_{21}$ and $R_{22}$ are described above.

The electron deficient group substituted 1,2-dioxetanes hereof correspond to the following:

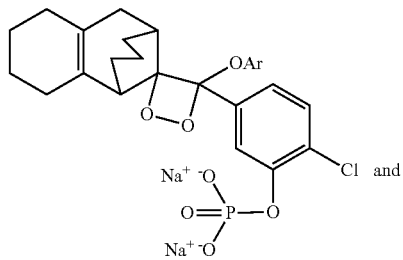

(20)

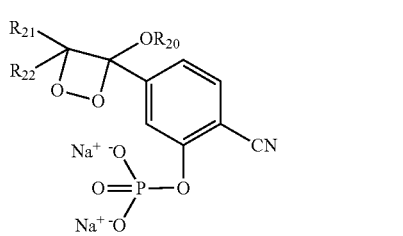

(21)

When these 1,2-dioxetanes react with alkaline phosphatase enzyme in an aqueous buffer, they give an unstable aryl oxide 1,2-dioxetane intermediates of the formulae:

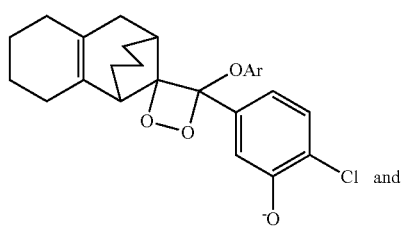

(22)

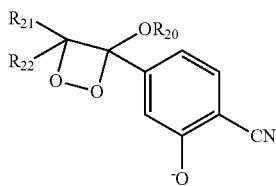
(23)

These unstable 1,2-dioxetanes intermediates (22) and (23), then, spontaneously decompose to produce light and compounds of the following formulae:

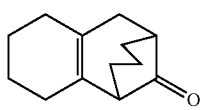
(18)

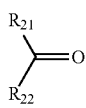
(24)

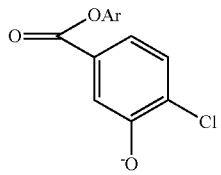
(25)

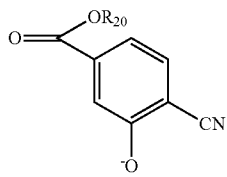
(26)

More particularly the 1,2-dioxetanes hereof are prepared from alkenes having an isotopic or nonisotopic hydrogen or isotopic or nonisotopic hydrogen atom-containing group thereof. These alkenes are prepared by the reaction of (a) a spiro-fused ketone with or without a π-electron in the ring or side chain or other ketone having a carbon to carbon double bond or triple bond with (b) an aromatic ester or other ketone, wherein at least one or both of the spiro-fused ketone or ester or other ketone has an isotopic hydrogen or isotopic hydrogen-containing group.

Generally, the reaction proceeds, using titanium trichloride or tetrachloride and a reducing agent such as an active metal or lithium aluminum hydride in tetrahydrofuran (THF) or other solvent of choice. This reaction is an intermolecular coupling of a ketone and an ester or ketone to form a vinyl ether using a modified McMurray procedure.

Ar is substituted or unsubstituted aromatic ring having electron withdrawing group or groups, $R_{20}$, $R_{21}$ and $R_{22}$ are described above. The new alkenes hereof used to prepare the present 1,2-dioxetanes, thus, correspond to the general formula:

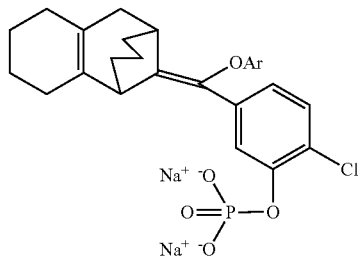
(27)

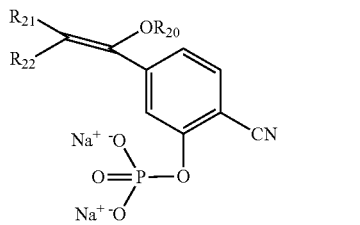
(28)

Generally, the intermolecular coupling reaction between the spiro-fused ketone or ketones and the ester or other ketone is carried out at a temperature ranging from about 25° C. to about 85° C. and, preferably, from about 45° C. to about 65° C.

After the alkene is obtained it is then, photooxidized to form the stable, triggerable 1,2-dioxetanes hereof. These dioxetanes can, then, be de-stablized or triggered by reaction with a base, an acid, enzyme and or inorganic or organic catalyst and/or electron donor source in the presence or absence of a fluorescent compound.

These electron withdrawing group containing 1,2-dioxetanes hereof can detect β-galactosidase enzyme at very low level. The substrates are prepared by the photooxidation of β-galactose-substituted alkenes which are prepared by reacting the hydroxy group containing alkenes on benzene ring such, as (3-hydroxy-4-cyanophenyl)methoxymethylene tricyclo[7.3.1.0$^{2,7}$]tridec-2,7-ene and [(3-Hydroxy-4-chlorophenyl)-2-methoxy (D$_3$) methylene]adamantane, with acetobromo-α-D-galactose.

Substrates for β-galactosidase enzyme are more sensitive then prior substrates due to the effect of the π-electrons on the decomposition of the 1,2-dioxetane intermediates in the form of phenoxide ion formed after the interaction of the galactoside group on the 1,2-dioxetane and the β-galactosidase enzyme. The effect of the cyano group on the phenoxide ion and the deuterated methyl group on the dioxetane ring, also, enhances the output of chemiluminescent light.

The enzymatic cleavage of both unsaturated and saturated 1,2-dioxetanes can be shown as:

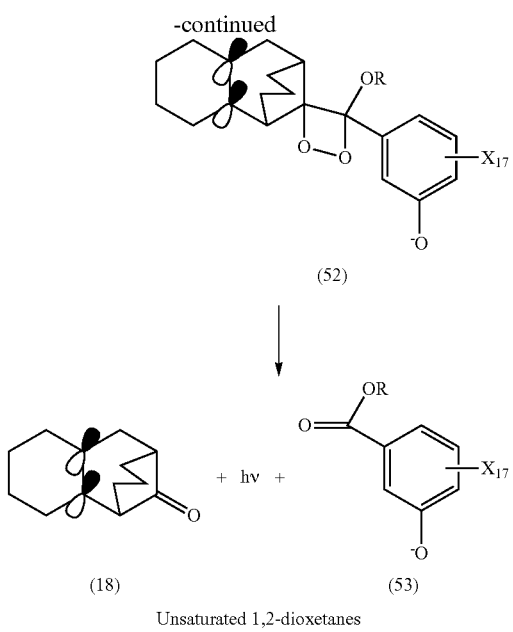

(52)

↓

(18)  (53)

Unsaturated 1,2-dioxetanes wherein $X_{17}$ is H, Cl, Br, CN; R is $CH_3$, $CD_3$.

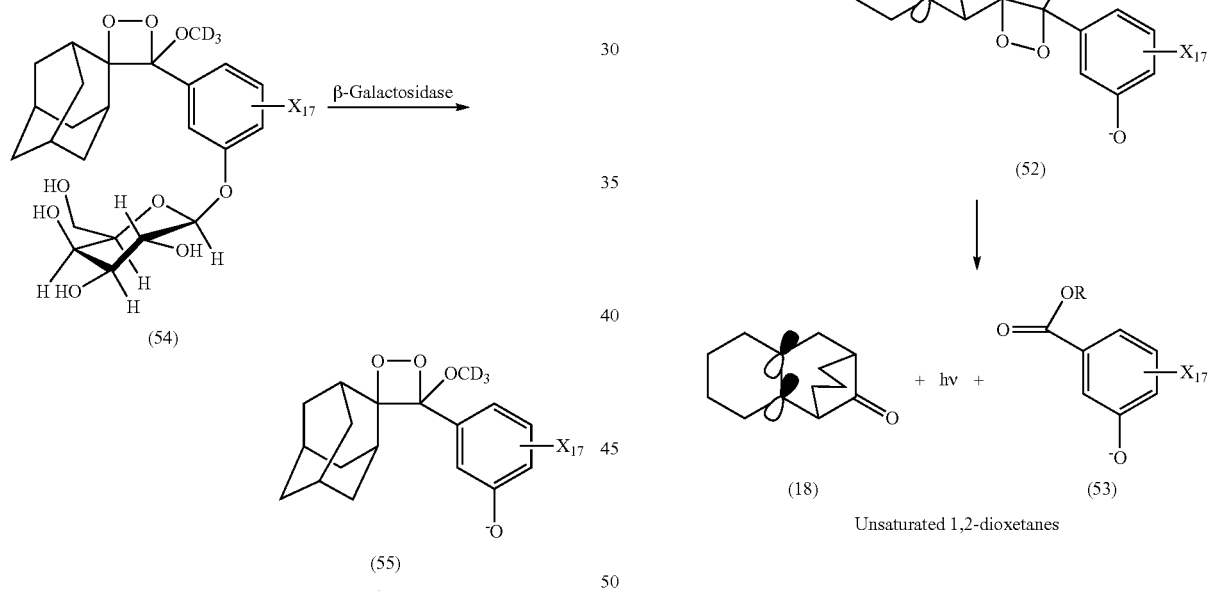

(54)

↓

(55)

↓

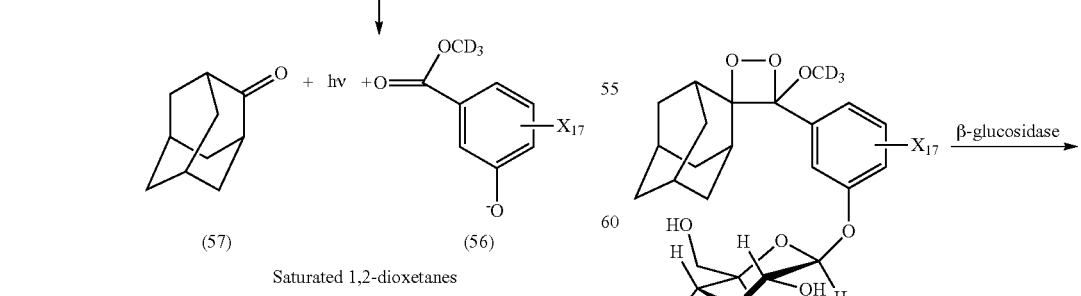

(57)  (56)

Saturated 1,2-dioxetanes wherein $X_{17}$ is H, Cl, Br, CN

Similarly the electron withdrawing 1,2-dioxetanes are useful substrates for β-glucosidase enzyme detection. They are prepared by the photooxidation of β-D-glucoside-substituted alkenes which, in turn, are prepared by the reaction of hydroxy group containing alkenes on benzene ring such as, (3-hydroxy-4-cyanophenyl)methoxymethylene tricyclo [7.3.1.0$^{2,7}$]tridec-2,7-ene and [(3-Hydroxy-4-chlorophenyl)-2-methoxy ($D_3$) methylene]adamantane and 2,3,4,6-tetra-O-acetyl-α-D-glucopyranosyl bromide, where the cleavage reaction proceeds as flows:

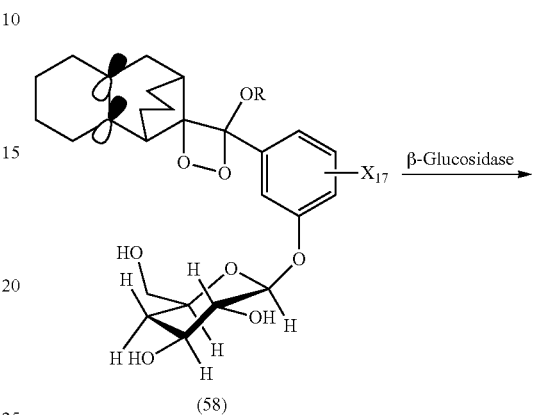

(58)

(52)

↓

(18)  (53)

Unsaturated 1,2-dioxetanes wherein $X_{17}$ is H, Cl, Br, CN; R is $CH_3$, $CD_3$.

(59)

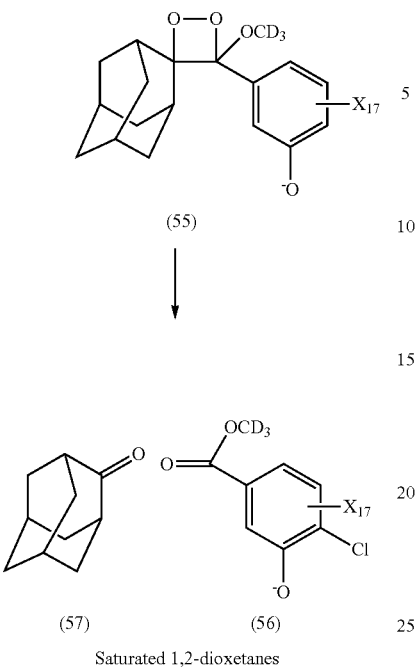

(55)

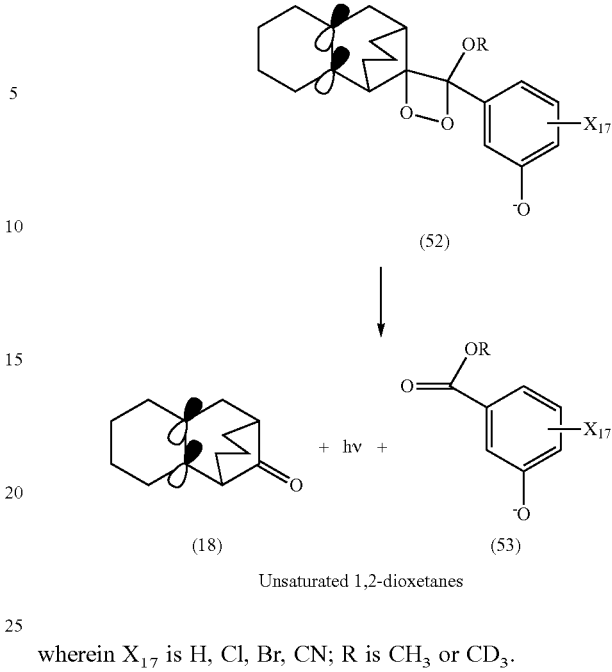

(52)

wherein $X_{17}$ is H, Cl, Br, CN; R is $CH_3$ or $CD_3$.

wherein $X_{17}$ is H, Cl, Br, CN

Using the same electron withdrawing 1,2-dioxetane (59), β-glucuronidase enzyme substrates are also provided prepared by the photooxidation of β-D-glucoside-substituted alkenes which, in turn, are prepared by the reaction hydroxy group containing alkenes on benzene ring such as, (3-hydroxy-4-cyanophenyl)methoxymethylene tricyclo[7.3.1.0$^{2,7}$]tridec-2,7-ene and [(3-Hydroxy-4-chlorophenyl)-2-methoxy (D$_3$) methylene]adamantane and acetobromo-α-D-glucoronic acid, methyl ester.

These chemiluminescent systems appear to be at least 1000 times more sensitive compared to the chromophoric substrates.

The enzymatic cleavage of the 1,2-dioxetane in the presence of β-glucuronidase enzyme can be shown as:

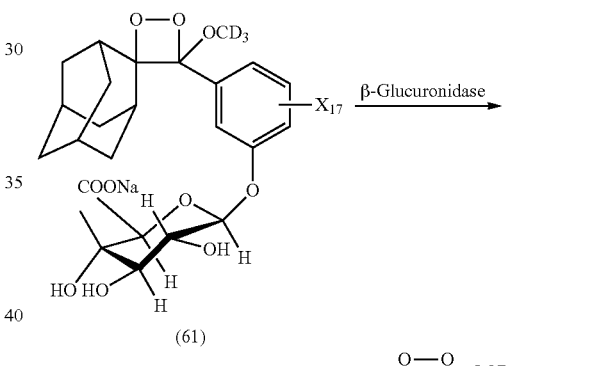

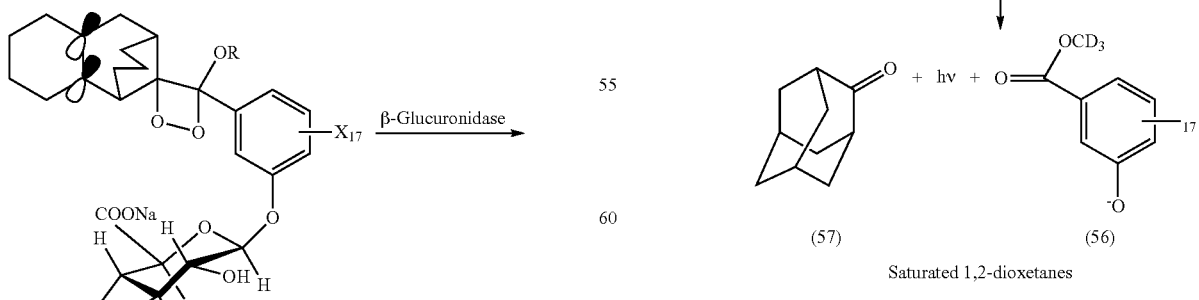

wherein $X_{17}$ is H, Cl, Br, CN

Also, arylesterase enzyme substrates prepared by the photooxidation of acetyl-substituted alkenes, which can be prepared by the reaction of reaction hydroxy group containing alkeneson benzene ring such as, (3-hydroxy-4-cyanophenyl)methoxymethylene tricyclo[7.3.1.0$^{2,7}$]tridec-2,7-ene and [(3-Hydroxy-4-chlorophenyl)-2-methoxy (D$_3$) methylene]adamantane and acetyl chloride reaction.

The enzymatic cleavage of these same electron withdrawing group containing 1,2-dioxetanes can be shown as:

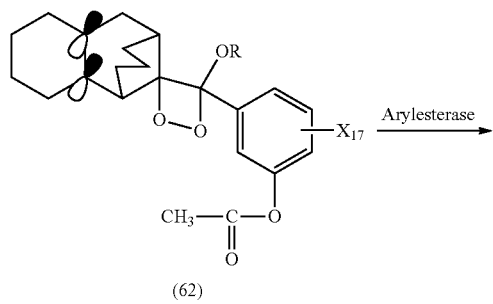

(62)

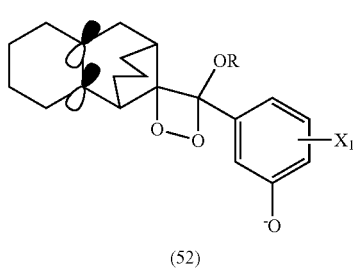

(52)

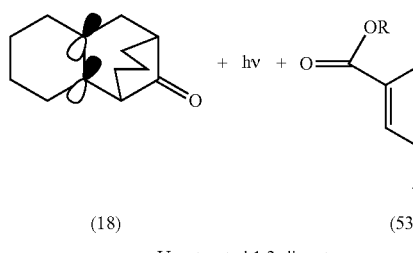

(18)      (53)

Unsaturated 1,2-dioxetanes wherein X$_{17}$ is H, Cl, Br, CN; R is CH$_3$, CD$_3$.

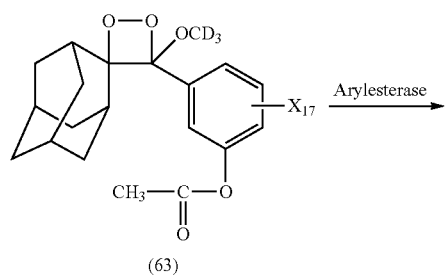

(63)

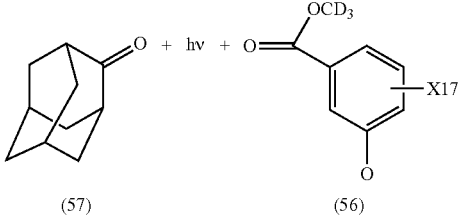

(55)

(57)    (56)

Saturated 1,2-dioxetanes wherein X$_{17}$ is H, Cl, Br, CN

The same applied for arylsulfatase enzyme substrates where the sulfate-substituted alkenes are prepared by the reaction of hydroxy group containing alkenes on benzene ring such as, (3-hydroxy-4-cyanophenyl)methoxymethylene tricyclo[7.3.1.0$^{2,7}$]tridec-2,7-ene and [(3-Hydroxy-4-chlorophenyl)-2-methoxy (D$_3$) methylene]adamantane and chlorosulfonic acid. The enzymatic cleavage of electron withdrawing group containing 1,2-dioxetane can be shown as:

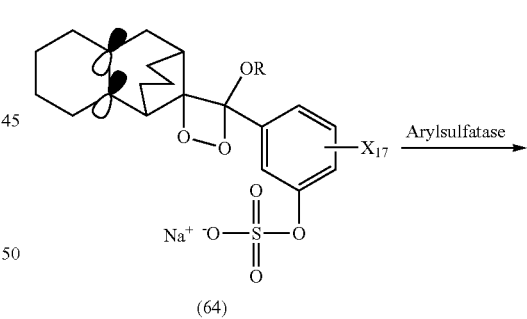

(64)

(52)

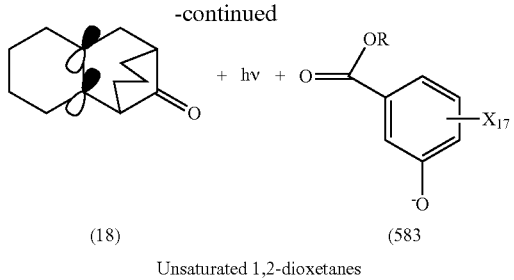

(18)                          (583)

Unsaturated 1,2-dioxetanes wherein $X_{17}$ is H, Cl, Br, CN; R is $CH_3$, $CD_3$.

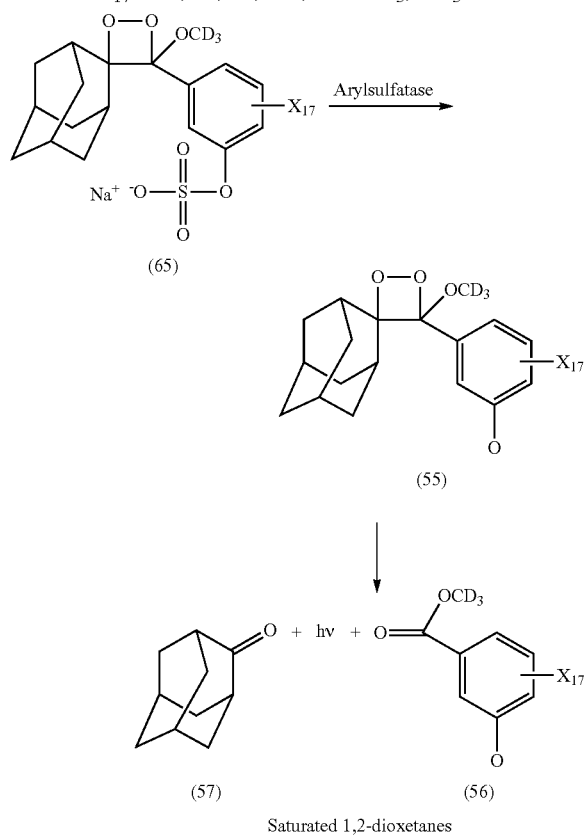

Saturated 1,2-dioxetanes wherein $X_{17}$ is H, Cl, Br, CN

Tethered bis-1,2-dioxetanes

A second class of new 1,2-dioxetanes are tethered bis-1,2-dioxetanes. These tether bis-1,2-dioxetanes are prepared by the photo-oxidation of tethered bis-alkenes.

The bis-1,2-dioxetanes hereof generally correspond to the formula:

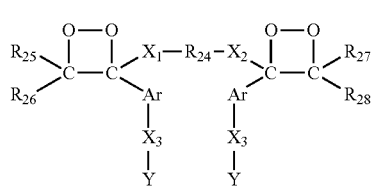

(8)

$X_1$, $X_2$ and $X_3$ are each individually, sulphur or oxygen or nitrogen; $R_{24}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{25}$ and $R_{26}$ (I) form (R)

which is a cyclic, polycyclic or spiro-fused ring containing at least one carbon-carbon double bond or cabon-carbon triple bond in the ring or side chain, with or without heteroatoms, or (II) form (Ar)

which is a cyclic, polycyclic or a spiro-fused ring containing a substituted or unsubstituted fused aromatic ring or a substituted or unsubstituted aromatic ring attached by linker arms, or (III) form (R)

which is either a cyclic, substituted or unsubstituted polycyclic alkyl group which is spiro-fused to the dioxetane ring or (IV) are each substituted or unsubstituted branched alkyl groups or cycloalkyl groups having 3 to 8 carbon atoms and being substituted in the ring or side chain, Ar is either phenyl, substituted phenyl, naphthyl, substituted naphthyl, anthryl, substituted anthryl with or without a fluorescent group; Y is either hydrogen, alkyl, acetate, t-butyldimethylsilyl, an enzyme cleavable group or an antibody cleavable group; and $R_{24}$ is an organic group having an isotopic hydrogen (deuterium atom) and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{27}$ and $R_{28}$ are the same as $R_{25}$ and $R_2$, wherein individually $R_{24}$, $R_{25}$, $R_{26}$, $R_{27}$, $R_{28}$ and Ar may be a deuterium atom or deuterium atom containing organic group; or

II

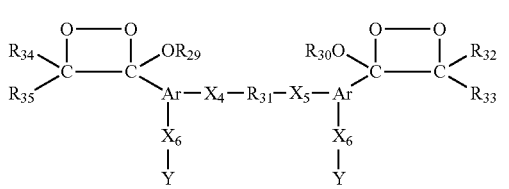
(9)

$X_4$, $X_5$ and $X_6$ are each individually sulphur, oxygen or nitrogen; $R_{29}$ and $R_{30}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{32}$ and $R_{33}$ (I) form

which is a cyclic, polycyclic or spiro-fused ring containing at least one carbon-carbon double bond or cabon-carbon triple bond in the ring or side chain, with or without heteroatoms, or (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) are each substituted or unsubstituted branched alkyl groups or cycloalkyl groups having 3 to 8 carbon atoms and being substituted in the ring or side chain, Ar is either phenyl, substituted phenyl, naphthyl, substituted naphthyl, anthryl, substituted anthryl with or without a fluorescent group; Y is either hydrogen, alkyl, acetate, t-butyldimethylsilyl, an enzyme cleavable group, or an antibody cleavable group; and $R_{31}$ is a aryl or alkyl linker arm; $R_{34}$ and $R_{35}$ are as described above for $R_{32}$ and $R_{33}$
or

III

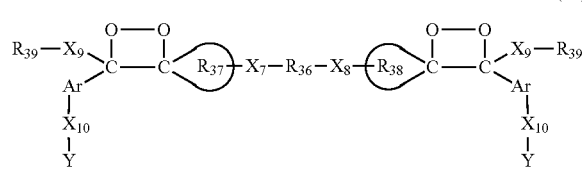
(10)

wherein $R_{36}$, $R_{37}$, $R_{38}$, $R_{39}$ and Ar may include a deuterium atom or deuterium atom containing organic group; $X_7$, $X_8$, $X_9$ and $X_{10}$ are each individually sulphur, oxygen or nitrogen, Y is either hydrogen, alkyl, acetate, t-butyldimethylsilyl, an enzyme cleavable group, or an antibody cleavable group; $R_{36}$ is an aryl or alkyl linker arm; $R_{39}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; $R_{37}$ (I) form

which is a cyclic, polycyclic or spiro-fused ring containing at least one carbon-carbon double bond or cabon-carbon triple bond in the ring or side chain, with or without heteroatoms, (II) form

which is a cyclic, polycyclic or a spiro-fused ring containing a substituted or unsubstituted fused aromatic ring or a substituted or unsubstituted aromatic ring attached by linker arms, or (III) form

which is either a cyclic, substituted or unsubstituted polycyclic alkyl group which is spiro-fused to the dioxetane ring or (IV) a substituted or unsubstituted branched alkyl groups or cycloalkyl groups having 3 to 8 carbon atoms and being substituted in the ring or side chain; $R_{38}$ is as described above for $R_{37}$, wherein individually $R_{29}$, $R_{30}$, $R_{31}$, $R_{32}$, $R_{33}$, $R_{34}$, $R_{35}$ and Ar may comprise a deuterium atom or deuterium atom containing organic group;

IV or 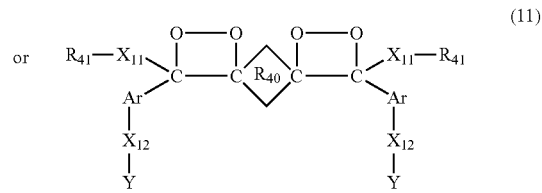
(11)

$X_{11}$ and $X_{12}$ are each, individually, sulphur, oxygen or nitrogen, Y is either hydrogen, alkyl, acetate, t-butyldimethylsilyl, an enzyme cleavable group, or an antibody cleavable group; $R_{40}$ (I) forms

which is a cyclic, polycyclic or spiro-fused ring containing at least one carbon-carbon double bond or cabon-carbon triple bond in the ring or side chain, with or without heteroatoms, or (II) forms

which is a cyclic, polycyclic or a spiro-fused ring containing a substituted or unsubstituted fused aromatic ring or a substituted or unsubstituted aromatic ring attached by linker arms, or (II) forms

which is either a cyclic, substituted or unsubstituted polycyclic alkyl group which is spiro-fused to the dioxetane ring or (IV) is a substituted or unsubstituted branched alkyl groups or cycloalkyl groups having 3 to 8 carbon atoms and being substituted in the ring or side chain; $R_{41}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl (etheralkyl)$_2$, alkyl(etheralkyl)$_3$, alkyletherhaloalkyl, alkyl (etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-flourescent molecule, linker-antibody, linker-antigen, linker-biotin, inker-avidin, linker-protein, linker-carbohydrate or linker-lipid; and Ar either phenyl, substituted phenyl, naphthyl, substituted naphthyl, anthryl, substituted anthryl with or without a fluorescent group, wherein each of $R_{40}$, $R_{41}$, and Ar may include a deuterium atom or deuterium atom containing organic group.

The bis-1,2-dioxetanes hereof are prepared from alkenes having an isotopic or nonisotopic hydrogen or isotopic or nonisotopic hydrogen atom-containing group thereof and correspond to the formula:

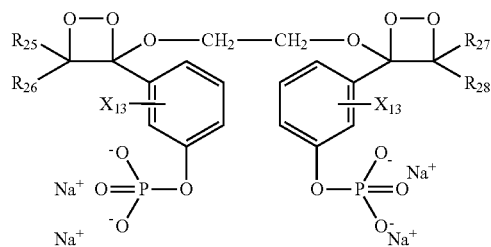

(29)

wherein $X_{13}$, $R_{25}$, $R_{26}$, $R_{27}$ and $R_{28}$ are as described above, or

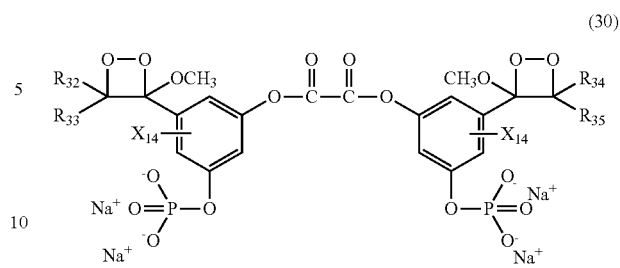

(30)

wherein $X_{14}$, R32, $R_{33}$, $R_{34}$ and $R_{35}$ as are describe above, or

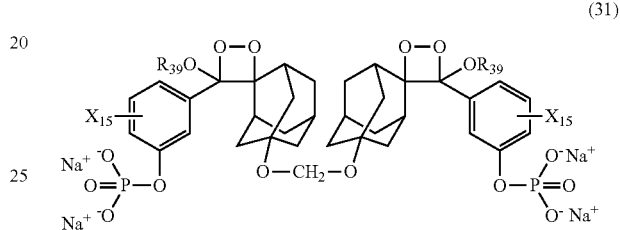

(31)

wherein $R_{39}$, and $X_{15}$ are as described above, or

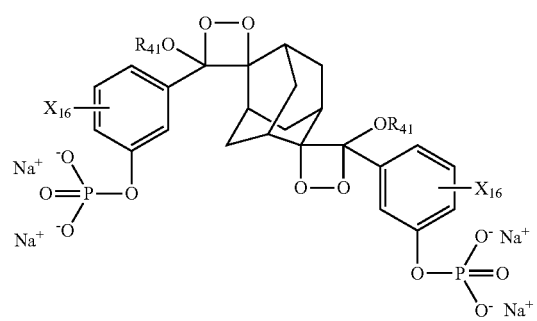

(32)

wherein $R_{41}$ and $X_{16}$ are as described above.

The bis-1,2-dioxetanes of formulae (29), (30), (31) and (32) react with alkaline phosphatase enzyme in an aqueous buffer. They breakdown into an unstable aryl oxide 1,2-dioxetane intermediate of the following formulae (33), (34), (35) and (36), respectively;

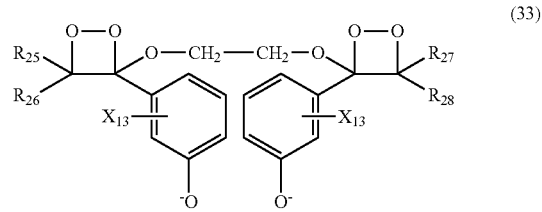

(33)

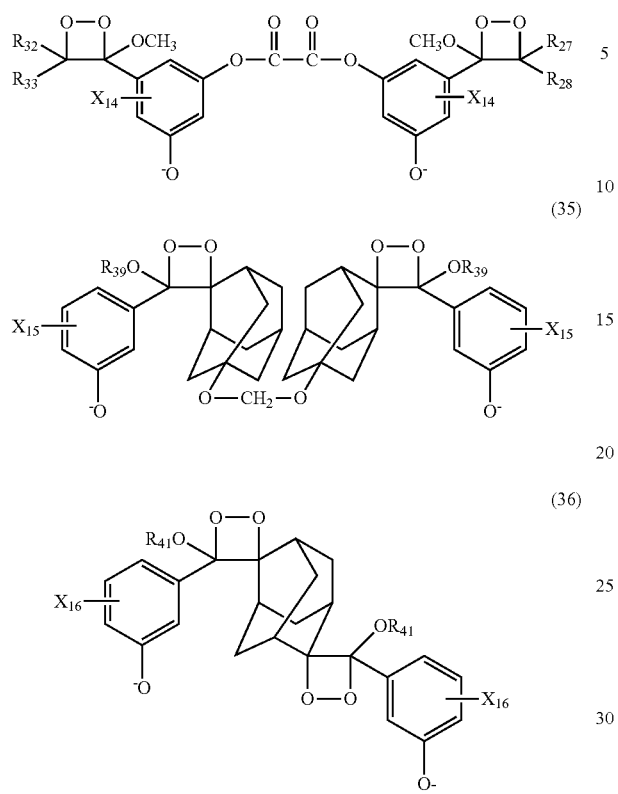

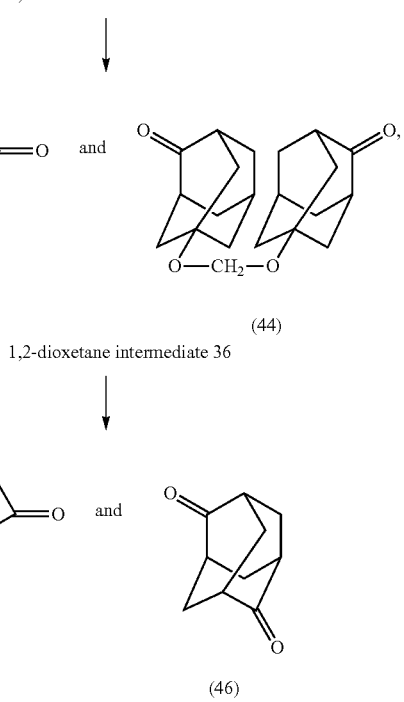

These unstable 1,2-dioxetane intermediates, then, spontaneously decompose to produce light and compounds of the formulae:

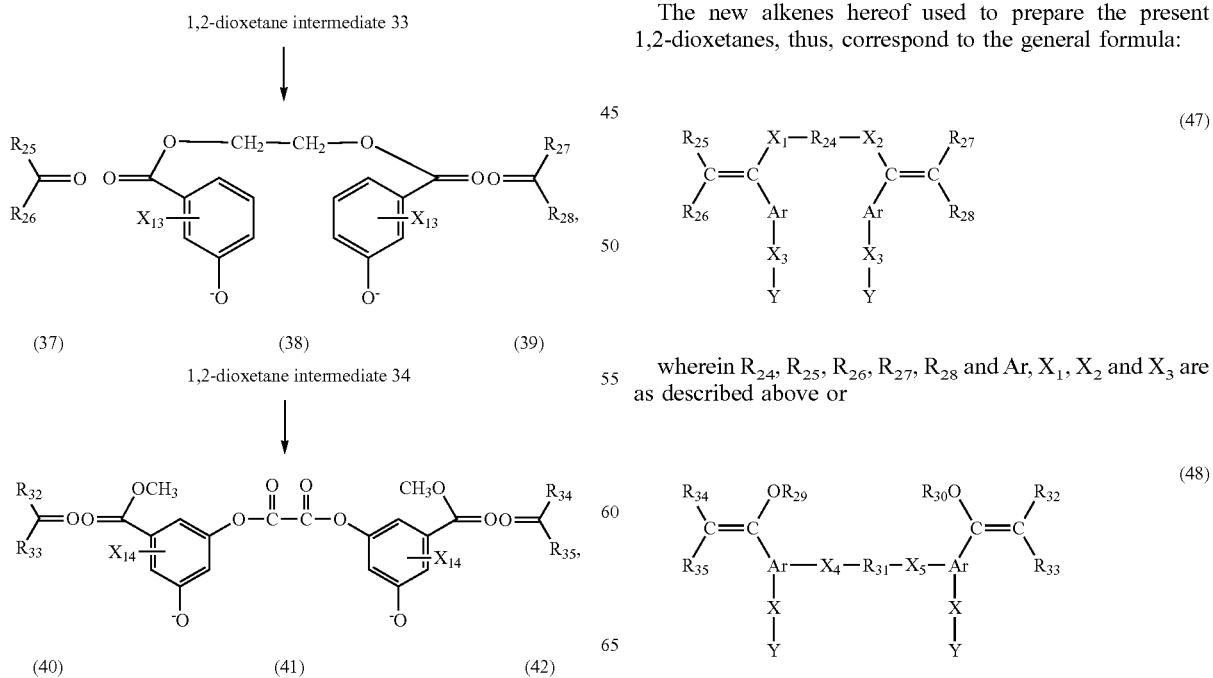

The intermediate alkenes for the synthesis of bis-1,2-dioxetanes are prepared by the reaction of (a) a spiro-fused bis-(ketone) with either π-electrons or a carbon-carbon double or triple bond(s) in the spiro-fused ring and (b) an aromatic ester or another ketone or (2) (a) a spiro-fused ketone and a bis-(aromatic ester) or other tethered bis-(ketones). Additionally, these new tethered bis-(1,2-dioxetanes) may have electron donating or withdrawing groups with or without one of the hydrogen atoms replaced by deuterium at the four-membered peroxide ring.

The new alkenes hereof used to prepare the present 1,2-dioxetanes, thus, correspond to the general formula:

wherein $R_{24}$, $R_{25}$, $R_{26}$, $R_{27}$, $R_{28}$ and Ar, $X_1$, $X_2$ and $X_3$ are as described above or wherein $R_{29}$, $R_{30}$, $R_{31}$, $R_{32}$, $R_{33}$, $R_{34}$, $R_{35}$ and Ar, $X_4$, $X_5$ and $X_6$ are as described above
or

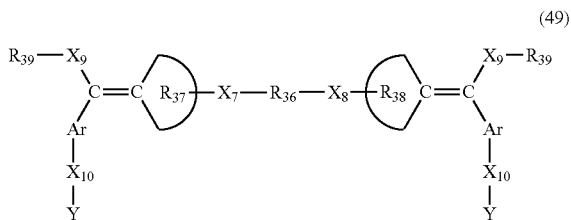
(49)

wherein $R_{36}$, $R_{37}$, $R_{38}$, $R_{39}$, $X_7$, $X_8$, $X_9$ and $X_{10}$ are as described above or

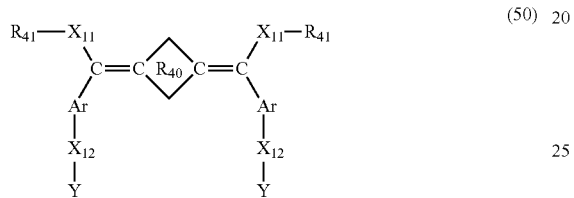
(50)

wherein $R_{40}$, $R_{41}$, and Ar, $X_{11}$, $X_{12}$ are as described above.

After the alkene is obtained it is then, photooxidized to form the stable, triggerable 1,2-dioxetanes hereof. These dioxetanes can, then, be de-stablized or triggered by reaction with a base, an acid, enzyme and or inorganic or organic catalyst and/or electron donor source in the presence or absence of a fluorescent compound.

For a more complete understanding of the present invention, reference is made to the following non-limiting examples. In the examples, all parts and percentages are by weight unless expressly stated to be otherwise.

In supporting the findings reported below, the structures of the resulting compounds were confirmed by Nuclear Magnetic Resonance (NMR). NMR spectra were recorded on a Brucker BZH 250 spectrometer in desired solvents using tetramethylsilane as an internal standard. Chemiluminescence kinetics was performed on a Berthold Microplate Luminometer at room temperature. The purity of the materials was checked by TLC on a silica gel plate. Melting points were measured in a MEL-TEMPII capillary melting point apparatus and are uncorrected. All the alkenes were dissolved in a suitable solvent and photo-oxidized by irradiation with a 1000 W sodium lamp under bubbled oxygen at ice-water temperature in the presence of polymer-bound Rose Bengal as reported in the literature.

Following are a series of examples illustrating the preparation of various acridanes in accordance with the present invention.

Example I

This Example Illustrates the Synthesis of phenyl 10-methyl ($D_3$) acridan-9-carboxylate Synthesis of methyl acridin-9-carboxylate (67)

Into a 100 mL round bottom flask equipped with magnetic stirrer and heating mantle was charged 5 parts of acridin-9-carboxylic acid hydrate (66) and 35 mL of thionyl chloride. The reaction mixture was heated at reflux for 3 hrs and gave reddish brown solution. Excess thionyl chloride was removed under reduced pressure and dried under vacuum to yield golden yellow solid which was dissolved in a solution of 2.82 parts of pyridine in 80 mL of dichloromethane under argon atmosphere and cooled to about 5° C. (ice-water). A solution of 2 parts of methanol in 20 mL of dichloromethane was added over 10 min to the solution and stirred for 30 min. The solution was stirred for 20 hrs and washed with 2×100 parts of deionized water. The organic layer was separated, dried over anhydrous $Na_2SO_4$ and filtered. The solution was concentrated under reduced pressure and purified by column chromatography on silica gel with 20% ethyl acetate-hexanes to yield, 4.32 parts of methyl acridin-9-carboxylate. NMR analysis showed the structure to the methyl acridin-9-carboxylate.

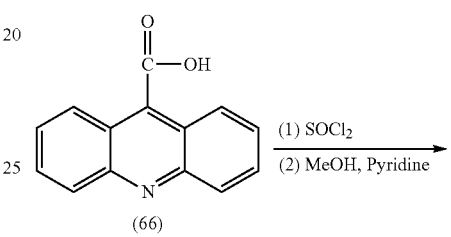
(66)

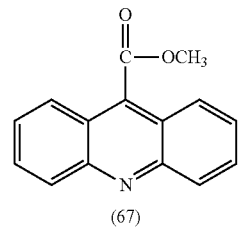
(67)

Synthesis of methyl 10-methyl ($D_3$) acridinium-9-carboxylate trifluoromethanesulfonate (68)

Thereafter into a 100 mL round bottom flask equipped with magnetic stirrer was charged a solution of 3.75 parts of the methyl acridin-9-carboxylate in 50 mL of dichloromethane under argon atmosphere. 5.8 parts of methyl ($D_3$) trifluoromethanesulfonate was added to the solution and stirred for 72 hrs at room temperature. A bright yellow solid was collected by filtration, washed with 2×5 mL of dichloromethane and air dried for 4 hrs to yield 66, 5.35 parts of methyl 10-methyl ($D_3$) acridinium-9-carboxylate trifluoromethanesulfonate.

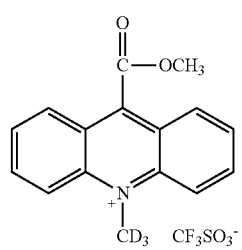
(68)

Synthesis of methyl 10-methyl (D$_3$) acridan-9-carboxylate (69)

Next, into a 500 mL round bottom flask equipped with magnetic stirrer, reflux condensor and heating mantle, under argon atmosphere, was charged 5.13 parts of the received acridinium salt (68) in 250 mL of ethanol. 19.5 parts NH$_4$Cl was added in six portions to a hot yellow solution, followed by 23.6 parts Zn in three portions causing immediate decolorization of the solution. The reaction mixture was refluxed for an additional 45 mins and filtered. The solid was washed with 2×40 mL of ethanol. The combined filtrate was concentrated under reduced pressure and yield an off-white solid. The solid was dissolved in 150 mL of dichloromethane and washed with 2×50 mL of deionized water. The organic layer was separated, dried over anhydrous Na$_2$SO$_4$ and filtered. The solution was concentrated under reduced pressure and 2.95 parts of methyl 10-methyl (D$_3$) acridan-9-carboxylate. NMR analysis showed the structure to the methyl 10-methyl (D$_3$) acridan-9-carboxylate.

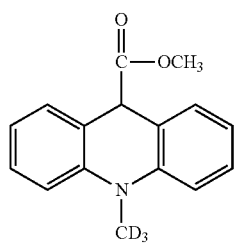

(69)

Synthesis of 10-methyl (D$_3$) acridan-9-carboxylic acid (70)

Thereafter into 500 mL round bottom flask equipped with magnetic stirrer, reflux condenser and heating mantle under argon atmosphere was charged a solution of 2.9 parts of methyl ester 69 in 200 mL of methanol. An aqueous solution of 5.3 N NaOH (9 mL) was added to the hot solution and heated at reflux for 6 hr. The solution was cooled to room temperature and concentrated under reduced pressure. The residue was dissolved in 50 mL of deionized water under an argon atmosphere. The pH was adjusted to 6.0 with 2.75 mL of CH$_3$CO$_2$H and dissolved in 100 mL of dichloromethane. The organic layer was separated, dried over anhydrous Na$_2$SO$_4$ and filtered. The solution was concentrated under reduced pressure and dried under vacuum to yield 2.45 parts of 10-methyl (D$_3$) acridan-9-carboxylic acid and the structure was identified by NMR.

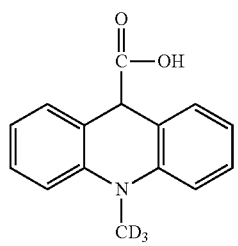

(70)

This 10-methyl (D$_3$) acridan-9-carboxylic acid (70) was used to prepare different acridanes carboxylates as described below:

Synthesis of 10-methyl (D$_3$) acridan-9-carboxylic acid chloride (71)

A solution of 0.24 Parts of 10-methyl (D$_3$) acridan-9-carboxylic acid in 15 mL of dichloromethane was charged into a 50 mL round bottom flask round bottom flask equipped with magnetic stirrer under an argon atmosphere and cooled tot 5° C. Next 0.76 parts of thionyl chloride was added to the cold yellow acid solution and stirred for 2 hrs at the temp below 15° C. The light red brown solution was then concentrated under reduced pressure and residue dried for 10 mins under reduced pressure.

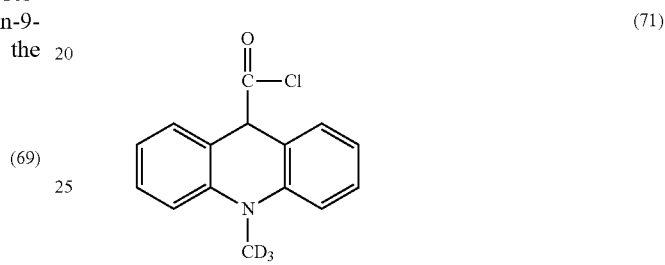

(71)

Synthesis of phenyl 10-methyl (D$_3$) acridan-9-carboxylate (72)

Next, into a 50 mL round bottom flask equipped with magnetic stirrer under an argon atmosphere was charged a solution of the acid chloride (71) prepared from above, 0.29 parts of diisopropylethylamine in 10 mL of dichloromethane and cooled at 5° C. (ice-water). A solution of 0.095 parts of phenol in 5 mL of dichloromethane and 1 mL of tetrahydrofuran was added to the mixture over 10 min to light brown acid chloride solution and stirred for 30 min. The cooling bath was removed and the reaction mixture was stirred at room temperature for 20 hr. The crude mixture was purified by column chromatography on silica gel with 20% ethyl acetate-hexanes to give phenyl 10-methyl (D$_3$) acridan-9-carboxylate (72), yield 0.155 parts, having the following structure confirmed by NMR.

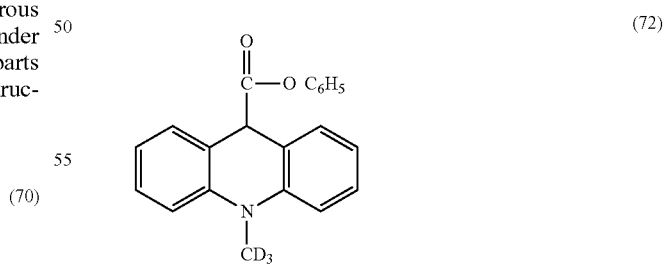

(72)

Example II

This example illustrates the synthesis of phenyl (D$_5$) 10-methyl (D$_3$) acridan-9-carboxylate:

The synthesis of phenyl (D$_5$) 10-methyl (D$_3$) acridan-9-carboxylate is achieved by following the same method as in Example I, using 0.48 parts of acid chloride (71) and 0.2 parts of deuterated phenol. The following structure of the isolated product, 0.275 parts, was confirmed by NMR.

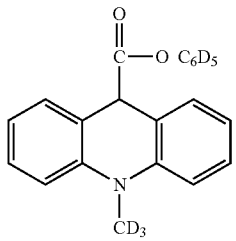
(73)

Example III

This example illustrates the synthesis of 2,2,2-Trifluoroethyl 10-methyl (D$_3$) acridan-9-carboxylate:

Following the same method as in Example 1,2,2,2-Trifluoroethyl 10-methyl (D$_3$) acridan-9-carboxylate was prepared from 0.48 parts of acid chloride (71) and 0.2 parts of 2,2,2-trifluoroethanol. The following structure of the isolated product, 0.275 parts, was confirmed by NMR.

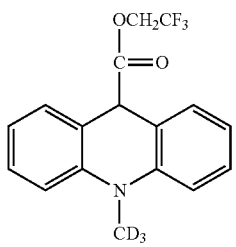
(74)

Example IV

This example illustrates the synthesis of phenyl (D$_5$) 10-methylacridan-9-carboxylate:

Synthesis of methyl 10-methylacridinium-9-carboxylate trifluoromethanesulfonate (75)

By reacting 4.2 parts of methyl acridin-9-carboxylate in 60 mL of dichloromethane and 6.4 Parts of methyl trifluoromethanesulfonate, as described in Example I, bright yellow solid was collected by filtration, washed with 2×5 mL of dichloromethane and air dried for 6 hr to give, 6.65 parts, of methyl 10-methylacridinium-9-carboxylate trifluoromethanesulfonate having the following structure.

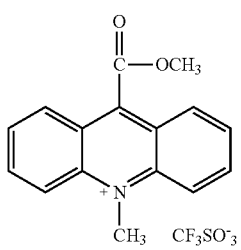
(75)

Synthesis of methyl 10-methylacridan-9-carboxylate (76)

A solution of methyl 10-methylacridinium-9-carboxylate trifluoromethanesulfonate (75), 4.25 parts, in methanol is reduced as described in Example I to give 3.2 parts of methyl 10-methylacridan-9-carboxylate and the isolated product has the following structure confirmed by NMR.

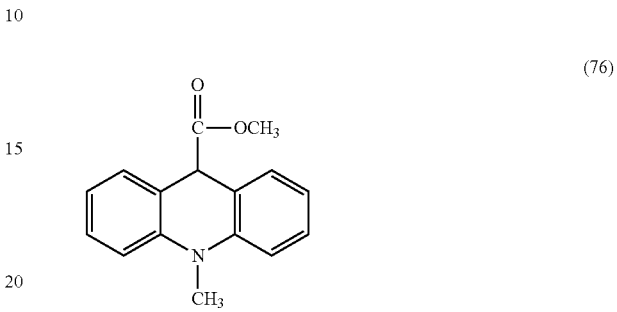
(76)

Synthesis of 10-Methylacridan-9-carboxylic acid (77)

A solutions of 3.2 parts of methyl ester (76) is hydrolyzed as described in Example I, to give 2.85 parts of 10-Methylacridan-9-carboxylic acid which was confirmed by NMR.

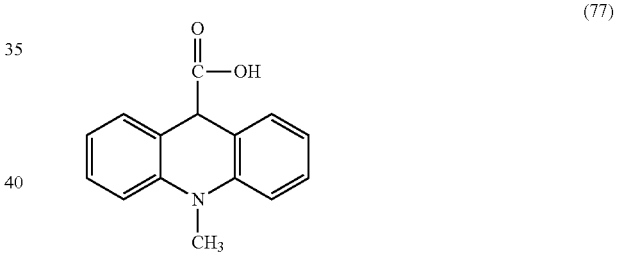
(77)

Synthesis of 10-Methylacridan-9-carboxylic acid chloride (78)

A solution of 0.35 parts of 10-methylacridan-9-carboxylic acid (77) in 20 mL dichloromethane and 1.1 parts of thionyl chloride is treated as described in Example I, to give 10-Methylacridan-9-carboxylic acid chloride.

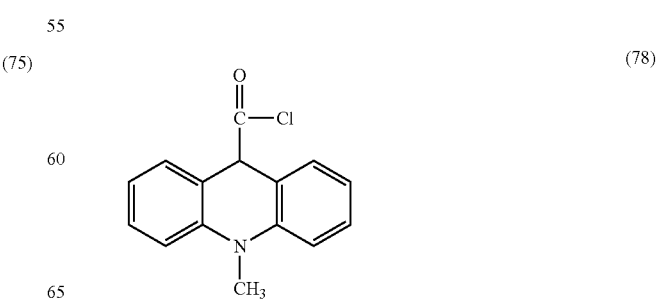
(78)

Synthesis of phenyl (D5) 10-methylacridan-9-carboxylate (79)

The acid chloride (78) prepared from above is treated with 0.5 parts of diisopropylethylamine in 15 mL of dichloromethane and 0.16 parts of phenol (D6) in 5 mL of dichloromethane and 1 mL of tetrahydrofuran as described in Example I to yield 0.24 parts of phenyl (D5) 10-methylacridan-9-carboxylate. The structure was confirmed by NMR as the following.

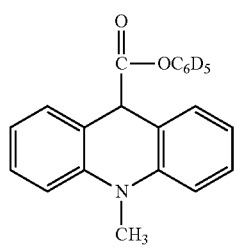

(79)

Example V

This example illustrates the synthesis of 4,4'-biphenyl 10-methylacridan-9-carboxylate (80):

A solution of 0.24 parts of 10-methylacridan-9-carboxylic acid chloride (78) in 10 mL dichloromethane and 0.145 parts of 4-phenylphenol (76) in 5 mL of dichloromethane and 1 mL of tetrahydrofuran is treated as described in example I, to give 0.21 parts of 4,4'-biphenyl 10-methylacridan-9-carboxylate. This compound has the following structure.

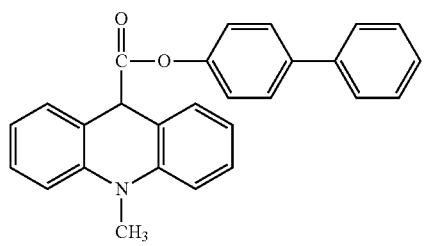

(80)

Example VI

This example illustrates the synthesis of [(4-Methoxy (D3))-4-(3-hydroxy-4-chlorophenyl)]spiro[1,2-dioxetane-3,2'-adamantane]-10-methylacridan-9-carboxylate:

A solution of 0.15 parts of 10-methyl(D3)acridan-9-carboxylic acid chloride (78) in 6 mL of dichloromethane and of 0.115 parts of [(4-Methoxy (D3))-4-(3-hydroxy-4-chlorophenyl)]spiro[1,2-dioxetane-3,2'-adamantane] in 2 mL of dichloromethane is treated as described in Example I, to give 0.134 parts of [(4-Methoxy (D3))-4-(3-hydroxy-4-chlorophenyl)]spiro[1,2-dioxetane-3,2'-adamantane]-10-methylacridan-9-carboxylate of the following structure confirmed by NMR.

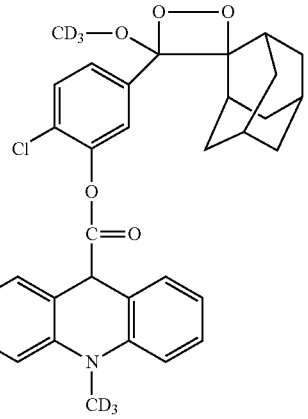

(81)

Example VII

This example illustrates the synthesis of [(4-Methoxy (D3)-4-(3-hydroxy-4-chlorophenyl)]spiro[1,2-dioxetane-3,13-tricyclo[7.3.1.0$^{2,7}$]tridec-2,7-ene]-10-methyl(D3)acridan-9-carboxylate:

A solution of a solution of 0.18 parts of 10-methyl(D3) acridan-9-carboxylic acid chloride (78) and of 0.115 parts of [(4-Methoxy (D3)-4-(3-hydroxy-4-chlorophenyl)]spiro[1,2-dioxetane-3,13-tricyclo[7.3.1.0$^{2,7}$]tridec-2,7-ene] in 2 mL of dichloromethane is treated, as described in example I, to give 0.13 parts of [(4-Methoxy (D3)-4-(3-hydroxy-4-chlorophenyl)]spiro[1,2-dioxetane-3,13-tricyclo[7.3.1.0$^{2,7}$]tridec-2,7-ene]-10-methyl(D3)acridan-9-carboxylate of the following structure confirmed by NMR.

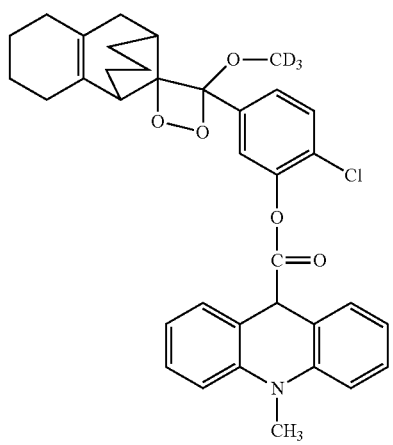

(81)

Example VIII

This example illustrates the synthesis of 4'-carboxylic acid-4-biphenyl 10-methylacridan-9-carboxylate:

A solution of a solution of 0.18 parts of 10-methylacridan-9-carboxylic acid chloride (78) and 0.2 parts of 4'-hydroxy-4-biphenylcarboxylic acid in 1 mL of pyridine is treated, as described in example I, to give 4'-carboxylic acid-4-biphenyl 10-methylacridan-9-carboxylate. 0.11 parts, of the following structure confirmed by NMR.

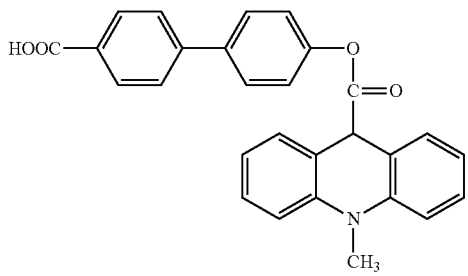

(82)

Example IX

This example illustrates the synthesis of [4-(2-propenoic acid)]phenyl-10-methyl-9-carboxylate:

Following the procedure of Example I, a solution of a solution of 0.235 parts of 10-methylacridan-9-carboxylic acid chloride (78) in 15 mL of dichloromethane and 0.22 parts of 4-hydroxycinnamic acid (87) in 1 mL of pyridine is treated to give 0.32 parts of [4-(2-propenoic acid)]phenyl-10-methyl-9-carboxylate, 0.13 parts, of the following structure confirmed by NMR.

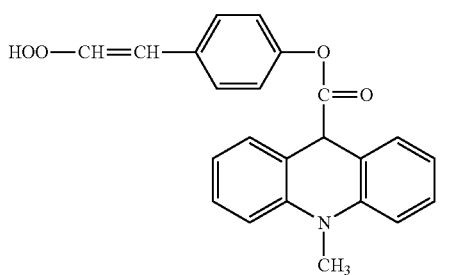

(83)

Example X

This example illustrates the synthesis of Bis-(1,2-Ethane) 10-methylacridan-9-carboxylate:

First, hydroxyethyl 10-methylacridan-9-carboxylate was prepared as follows:

Into a 50 mL round bottom flask equipped with magnetic stirrer and under an argon atmosphere was charged a solution of 0.305 parts of 10-methylacridan-9-carboxylic acid (77) in 15 mL of dichloromethane and cooled to 5° C. (ice-water). Then, 1.05 parts of thionyl chloride was added to the cold yellow acid solution and stirred for 1.5 hr at a temperature below 15° C. The light red brown solution was concentrated under reduced pressure and the residue was dried for 15 min to give acid chloride (78).

Then, into a round bottom flask equipped with magnetic stirrer under argon atmosphere was charged a solution of the acid chloride (78) prepared from above and 0.3 parts of diisopropylethylamine in 12 mL of tetrahydrofuran. This mixture was cooled in ice-water. A solution of 0.51 parts of ethylene glycol in 2 mL of tetrahydrofuran was added to the cold light brown acid chloride solution and stirred for 30 min. The cooling bath was removed and the reaction mixture was stirred for 20 hrs. The crude mixture was purified by column chromatography on silica gel with 20% ethyl acetate-hexanes to yield 0.21 parts of the following carbon/late.

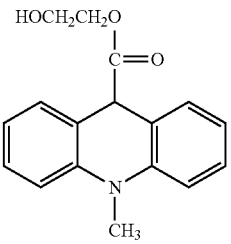

(84)

Thereafter bis-(1,2-Ethane) 10-methylacridan-9-carboxylate was prepared from the ester by the following procedure:

Into a 50 mL round bottom flask equipped with magnetic stirrer under argon atmosphere was charged the solution of 0.127 parts of 10-methylacridan-9-carboxylic acid (74) in 5 mL of dichloromethane and cooled to 5° C. Then 0.4 parts of thionyl chloride was added to the cold yellow acid solution and stirred for 2.25 hrs at a temperature below 15° C. The light red brown solution was concentrated under reduced pressure and residue dried for 40 min. following the procedure set forth in Example I, the resulting acid chloride (78) was used to react 0.1 parts of hydroxyethyl ester (84) in 1 mL of tetrahydrofuran to yield 0.072 parts bis-(1,2-ethane) 10-methylacridan-9-carboxylate and the following structure was confirmed by NMR.

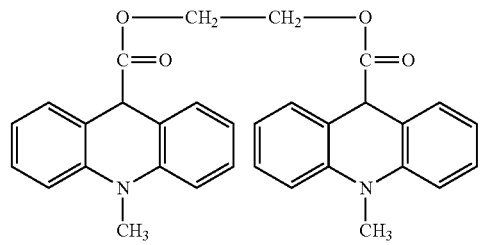

(85)

Example XI

This example illustrates the synthesis of bis-(1,4-phenoxy) 10-methylacridan-9-carboxylate (91):

First, 4-(tert-butyldimethylsilyloxy)phenol (93) was prepared by the following procedure:

A solution of 2.9 parts of imidazole, 1.99 parts of hydroquinone and 3 parts of tert-butyldimethylsilyl chloride in 10 mL of dimethylformamide was stirred at room temperature for 1 hr 45 min. The reaction was monitored by TLC showed formation of product. The reaction mixture was diluted with 50 mL of deionized water and product was extracted with 2×50 mL of ether. The combined organic layer was dried over anhydrous $Na_2SO_4$ and filtered. The filtrate was concentrated under reduced pressure and purified by column chromatography on silica gel with 5% ethyl acetate-hexanes to yield 2.24 parts 4-(tert-butyldimethylsilyloxy)phenol. NMR was used to confirm the following structure.

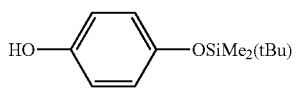
(86)

Thereafter 4-(tert-butyldimethylsilyloxy)phenyl acridin-9-carboxylate was prepared by the following procedure:

A solution of 1.2 parts of 4-silyloxyphenol (86) in 10 mL of dichloromethane was treated with acid chloride of acridinium-9-carboxylic acid (66) described in example I to yield 1.6 parts of 4-(tert-butyldimethylsilyloxy)phenyl acridin-9-carboxylate having the following structure confirmed by NMR.

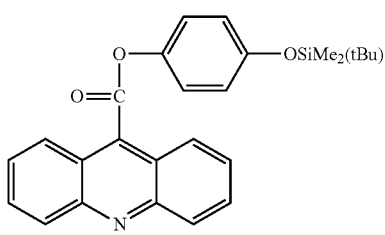
(87)

Then 4-(tert-butyldimethylsilyloxy)phenyl 10-methylacridinium-9-carboxylate trifluoromethanesulfonate was prepared as follows:

Into a 50 mL round bottom flask equipped with magnetic stirrer under argon atmosphere charged a solution of 1.6 parts of 4-(tert-butyldimethylsilyloxy)phenyl acridin-9-carboxylate in 25 mL of dichloromethane. 3.2 Parts of methyl trifluoromethanesulfonate was added to the solution and stirred for 40 hrs at room temperature. Bright yellow solid was collected by filtration, washed with 2×1 mL of dichloromethane and air dried for 4 hr to yield 1.44 parts of 4-(tert-butyldimethylsilyloxy)phenyl 10-methylacridinium-9-carboxylate trifluoromethanesulfonate having the following structure confirmed by NMR.

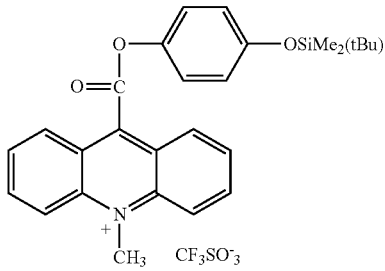
(88)

Thereafter 4-Hydroxyphenyl 10-methylacridan-9-carboxylate was prepared as follows:

Into a 50 mL round bottom flask equipped with magnetic stirrer, reflux condensor and heating mantle under an argon atmosphere was charged a solution of 1.42 parts of the 4-(tert-butyldimethylsilyloxy)phenyl 10-methylacridinium-9-carboxylate trifluoromethanesulfonate in 200 mL of ethanol. Then 16 arts $NH_4Cl$ was added in five portions, followed by 19.3 parts of Zn in five portions to a hot yellow solutions causing immediate decolorization of the solution. The reaction mixture was refluxed for 2 hrs and filtered. The solid was washed with 2×25 mL of ethanol. The combined filtrate was concentrated under reduced pressure to give off-white solid. The solid was dissolved in 250 mL of dichloromethane and washed with 100 mL of deionized water. After separation the organic layer was dried over anhydrous $Na_2SO_4$ and filtered. The solution was concentrated under reduced pressure and purified by column chromatography on silica gel with 10% ethyl acetate-hexane to yield 0.76 parts of 4-Hydroxyphenyl 10-methylacridan-9-carboxylate. The structure was confirmed as:

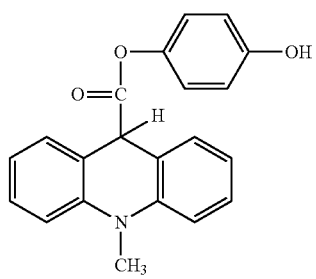
(89)

Thereafter bis-(1,4-phenoxy) 10-methylacridan-9-carboxylate was prepared by the following method:

A solution of 0.128 parts of 10-methylacridan-9-carboxylic acid chloride (75) in 8 mL of dichloromethane containing 0.15 parts of diisopropylethylamine was treated with the solution of 0.135 parts of 4-hydroxyphenyl acridan ester (96) in 3 mL of dichloromethane as described in example I to yield 0.126 parts bis-(1,4-phenoxy) 10-methylacridan-9-carboxylate and the structure was confirmed by NMR.

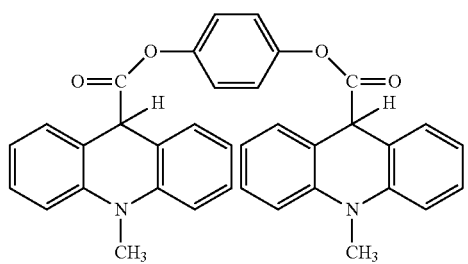
(90)

Example XII

This example illustrates the synthesis of bis-(1,5-naphthyl) 10-methylacridan-9-carboxylate:

A solution of 0.157 parts of 10-methylacridan-9-carboxylic acid chloride (78) in 10 mL dichloromethane and 0.067 parts of 1,5-dihydroxynaphthol (97) was reacted as described in Example I, to yield 0.1 parts bis-(1,5-naphthyl) 10-methylacridan-9-carboxylate. The following structure was confirmed by NMR.

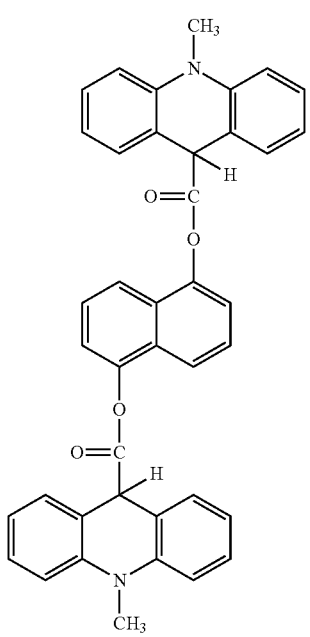

(91)

Following are a series of examples illustrating the preparation of 1,2-dioxetanes in accordance with the present invention.

Example XIII

This example illustrates the synthesis of [(4-phenoxy)-4-(3-phosphoryloxy-4-chlorophenyl)]spiro[1,2-dioxetane-3,13'-tricyclo[7.3.1.0$^{2,7}$]tridec-2,7-ene, disodium salt:

This compound was synthesized by the following procedure:

(a). Synthesis of tert-butyldimethylsilyl 3-tert-butyldimethylsilyloxybenzoate (92)

Into a 500 mL round bottom flask was charged a solution of 13.95 parts of 4-chloro-3-hydroxy benzoic acid, 33.5 parts of tert-butyldimethylsilyl chloride and 31.3 parts of imidazole in 31 mL of dry dimethylformamide and stirred at room temperature for 24 hr. The reaction was monitored by TLC on a silica gel plate showed formation of product. The reaction mixture was diluted with 250 mL of deionized water and the product was extracted with 2×250 mL of hexanes. The hexanes layer was washed with 3×200 mL deionized water, dried over anhydrous Na$_2$SO$_4$ and filtered. The solvent was evaporated under reduced pressure to yield 37.6 parts of an oil.

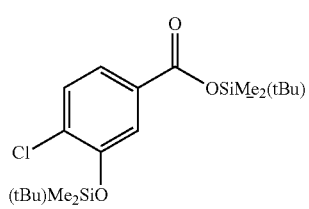

(92)

(b). Synthesis of 3-tert-Butyldimethylsilyloxybenzoic acid

Into a 500 mL round bottom flask, 38 mL of 10% aqueous NaOH solution was added over 5 min to a solution of 37.6 parts of tert-butyldimethylsilyl 3-tert-butyldimethylsilyloxybenzoate in 185 mL of tetrahydrofuran and the reaction mixture was stirred for 40 min at room temperature. The reaction was monitored by TLC on a silica gel plate showed formation of product. The reaction mixture was concentrated under reduced pressure and purified by column chromatography on silica gel using 30% ethyl acetate-hexanes to give an oil, yield 20.3 parts.

(93)

(c). Synthesis of 3-tert-Butyldimethylsilyloxybenzoyl chloride

Into a 100 mL round bottom flask a mixture of 5 parts of 3-tert-butyldimethylsilyloxybenzoic acid and 25 mL of thionyl chloride was heated at reflux for 1 hr 30 min. The reaction mixture was concentrated under reduced pressure to yield 5.77 parts of an oil.

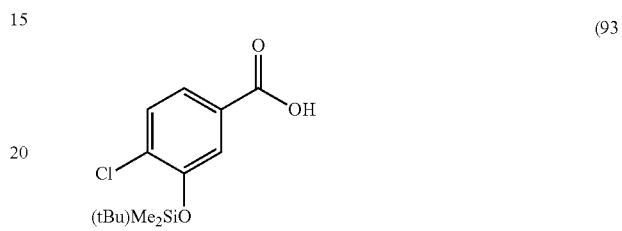

(94)

(d). Synthesis of phenyl 4-chloro-3-tert-butyldimethylsilyloxy benzoate

Into a 250 mL three neck round bottom flask equipped with magnetic stirrer and pressure-equalizing addition funnel under an argon atmosphere was charged a solution of 5.61 parts of 4-chloro-3-tert-butyldimethylsilyloxybenzoyl chloride and 2.12 parts of pyridine in 50 mL of dichloromethane and cooled to 5° C. (ice-water). A solution of 1.82 parts of phenol in 25 mL of dichloromethane was added drop-wise over 20 mins to a cold solution and stirred for additional 10 mins. The reaction mixture was stirred at room temperature for 4 hrs. The reaction was monitored by TLC on a silica gel plate showed formation of product. The reaction mixture was diluted with 125 mL of dichloromethane and was washed with 3×100 mL of deionized water. The organic layer was dried over anhydrous Na$_2$SO$_4$ and filtered. After evaporating the solvent, the crude mixture was purified by chromatography on silica gel with 10% ethylacetate-hexanes. The product fractions (TLC) were combined and evaporated under reduced pressure to give an oil, yield 4.9 parts.

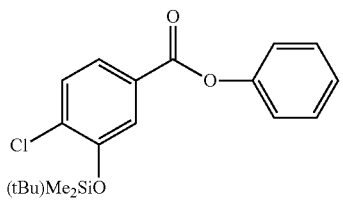

(95)

(e). Synthesis of (3-tert-butyldimethylsilyloxy-4-chlorophenyl)phenoxymethylene tricyclo[7.3.1.0$^{2,7}$]tridec-2,7-ene Into a 1 L three-neck flask equipped with mechanical stirrer, reflux condenser and pressure-equalizing addition funnel under nitrogen atmosphere was charged 150 mL of anhydrous tetrahydrofuran. 27.6 parts of TiCl$_4$ was added dropwise over 7 min and the suspension was stirred for 8 minutes. Then 22.8 parts of Zn dust was added carefully in small portions over 10 min to the suspension. The reaction mixture was heated at reflux for 4 hrs and 90 mL of Et$_3$N was added drop-wise over 10 mins. After refluxing the mixture for 50 mins, a solution of 4.9 parts of phenyl 4-chloro-3-tert-butyldimethylsilyloxy benzoate and 3.1 parts of ketone 18 in 100 mL anhydrous tetrahydrofuran was added drop wise over 1 hr 20 mins and refluxed for next 6 hrs. The mixture was cooled to room temperature and diluted with 500 mL 1:1 mixture of ethyl acetate-hexanes. The mixture was filtered and the solid was washed with 3×100 mL 1:1 solvent mixture. The combined filtrate was evaporated under reduced pressure and the crude mixture was purified by chromatography on a silica gel eluting with an ethyl acetate-hexane mixture containing 0.25% Et$_3$N. The product fractions (TLC) were combined and evaporated under reduced pressure to give an oil, yield 2.35 parts.

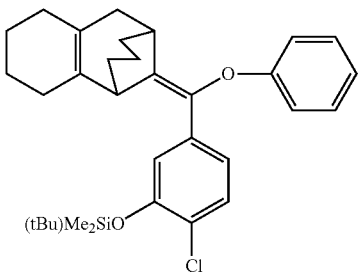

(96)

(f). Synthesis of (3-hydroxy-4-chlorophenyl)phenoxymethylene tricyclo[7.3.1.0$^{2,7}$]tridec-2,7-ene Into a 100 mL round bottom flask 1.62 parts of 75 wt. % solution of tetrabutylammonium fluoride in water was added over 2 min to a solution of 2.32 parts of pure (3-tert-butyldimethylsilyloxy-4-chlorophenyl)phenoxymethylene tricyclo[7.3.1.0$^{2,7}$]tridec-2,7-ene in 50 mL of tetrahydrofuran and stirred at room temperature for 2 hr. The reaction was monitored by TLC on a silica gel plate showed formation of product. The reaction mixture was evaporated under reduced pressure and extracted with 100 mL of dichloromethane. The organic layer was dried over anhydrous Na$_2$SO$_4$ and filtered. The solvent was evaporated under reduced pressure and crude mixture was purified by chromatography on silica gel with 25% ethyl acetate-hexanes containing 0.25% Et$_3$N. The product fractions (TLC) were combined and evaporated under reduced pressure to give an oil, yield 1.62 parts.

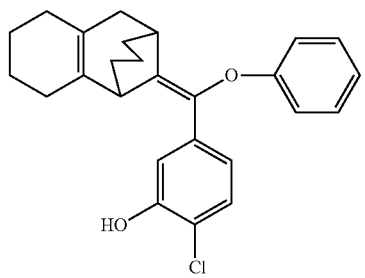

(97)

(g). Synthesis of (3-phosphoryloxy-4-chlorophenyl)phenoxymethylene tricyclo[7.3.1.0$^{2,7}$]tridec-2,7-ene, disodium salt Into a 250 mL three-neck round bottom flask equipped with magnetic stirrer and pressure equalizing addition funnel under argon atmosphere was added a solution of 1.79 parts of phosphorous oxychloride in 30 mL of dichloromethane and cooled to 5° C. Then, a solution of (3-hydroxy-4-chlorophenyl)phenoxymethylene tricyclo[7.3.1.0$^{2,7}$]tridec-2,7-ene and 3.3 parts of anhydrous pyridine in 20 mL of dichloromethane was added to the cold solution over 2 hr 10 min. The reaction mixture was stirred at room temperature for 3 hrs. The reaction was monitored by TLC on a silica gel plate and showed formation of a product. The reaction mixture cooled to 5° C. and a solution of 2.15 parts of 3-hydroxypropionitrile and 3.6 parts of anhydrous pyridine in 35 mL dichloromethane was added drop wise to the reaction mixture over 30 mins. The reaction mixture was stirred for 26 hrs at room temperature and was cooled to 5° C. for 45 mins and the solid was filtered and washed with cold 10 mL cold dichloromethane. The solvent was evaporated under reduced pressure and crude mixture was purified by chromatography on silica gel with 75% ethyl acetate-hexane containing 0.25% Et$_3$N. The product fractions (TLC) were combined and the solvent was evaporated under reduced pressure to give an oil, yield 1.42 parts. The phosphate ester was dissolved in 75 mL of acetone and 2.2 mL of 10% aqueous NaOH solution was added drop wise over 2 min. Stirring was continued for 2 hrs and the mixture was diluted with 20 mL of acetonitrile. The solid was filtered and washed with 5 mL of acetone. The solid material was crystallized from a methanol and acetone mixture. The solid was filtered, washed with 5 mL acetone and dried, yield 1.1 parts.

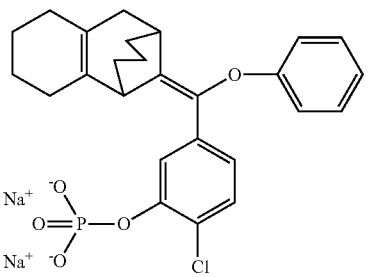

(98)

(h). Synthesis of [(4-phenoxy)-4-(3-phosphoryloxy-4-chlorophenyl)]spiro[1,2-dioxetane-3,13'-tricyclo[7.3.1.0$^{2,7}$]tridec-2,7-ene, disodium salt Disodium phosphate ester of (3-phosphoryloxy-4-chlorophenyl)phenoxymethylene tricyclo[7.3.1.0$^{2,7}$]tridec-2,7-ene, disodium salt was photo-oxidized as reported described to give [(4-phenoxy)-4-(3-phosphoryloxy-4-chlorophenyl)]spiro[1,2-dioxetane-3,13'-tricyclo[7.3.1.0$^{2,7}$]tridec-2,7-ene, disodium salt.

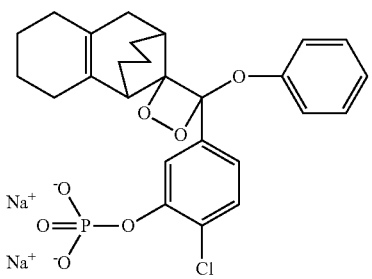

(99)

Example XIV

This example illustrates the synthesis of [4-(4-chlorophenoxy)-4-(3-phosphoryloxy-4-chlorophenyl)]spiro[1,2-dioxetane-3,13'-tricyclo[7.3.1.0$^{2,7}$]tridec-2,7-ene, disodium salt: This compound was synthesized by the following procedure:

(a). Synthesis of 4-Chlorophenyl 4-chloro-3-tert-butyldimethylsilyloxy benzoate

A solution of 5.75 parts of 4-chloro-3-tert-butyldimethylsilyloxybenzoyl chloride and 2.15 parts of pyridine in 50 mL of dichloromethane and 2.52 parts of 4-chlorophenol in 25 mL of dichloromethane was treated as described in example XIII (d) to give an oil, yield 5.5 parts and the following structure was confirmed by NMR.

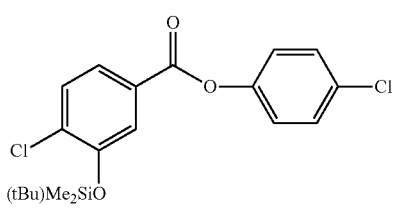

(100)

(b) Synthesis of (3-tert-butyldimethylsilyloxy-4-chlorophenyl) 4-chlorophenoxymethylene tricyclo[7.3.1.0$^{2,7}$]tridec-2,7-ene Similar method was used by using 5.3 parts of 4-Chlorophenyl 4-chloro-3-tert-butyldimethylsilyloxy benzoate and 3.25 parts of ketone 18 in 75 mL anhydrous tetrahydrofuran as described in example XIII (e) to give an oil, yield 2.4 parts. NMR spectrum was in agreement with the following structure.

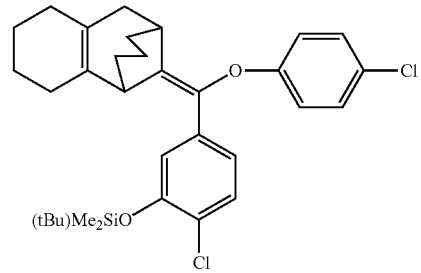

(101)

(c). Synthesis of (3-hydroxy-4-chlorophenyl) 4-chlorophenoxymethylene tricyclo[7.3.1.0$^{2,7}$]tridec-2,7-ene For the removal of siloxy group 1.6 parts of 75 wt. % solution of tetrabutylammonium fluoride in water was added over 2 min to a solution of 2.38 parts of (3-tert-butyldimethylsilyloxy-4-chlorophenyl) 4-chlorophenoxymethylene tricyclo[7.3.1.0$^{2,7}$]tridec-2,7-ene in 40 mL of tetrahydrofuran and stirred at room temperature for 2 hrs. After work up as described in example XIII (f) obtained an oil, yield 1.53 parts having the following structure confirmed by NMR.

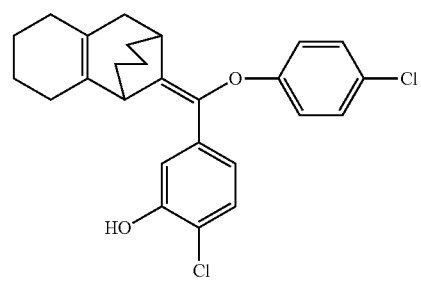

(102)

(d). Synthesis of (3-phosphoryloxy-4-chlorophenyl) 4-chlorophenoxymethylene tricyclo[7.3.1.0$^{2,7}$]tridec-2,7-ene, disodium salt was achieved by following the method, as described in Example XIII (g), In this reaction 1.5 parts of the (3-hydroxy-4-chlorophenyl) 4-chlorophenoxymethylene tricyclo[7.3.1.0$^{2,7}$]tridec-2,7-ene and 1.35 parts of (3-phosphoryloxy-4-chlorophenyl) 4-chlorophenoxymethylene tricyclo[7.3.1.0$^{2,7}$]tridec-2,7-ene, disodium salt was obtained and the following structure was confirmed by NMR.

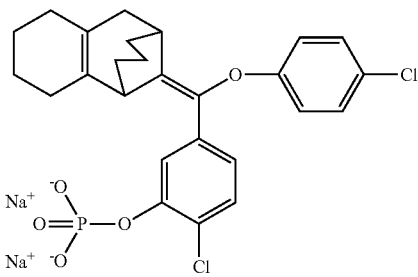

(103)

(e). Synthesis of [4-(4-chlorophenoxy)-4-(3-phosphoryloxy-4-chlorophenyl)]spiro[1,2dioxetane-3,13'-tricyclo[7.3.1.0$^{2,7}$]tridec-2,7-ene, disodium salt On photo-oxidation as described above, (3-phosphoryloxy-4-chlorophenyl) 4-chlorophenoxymethylenetricyclo [7.3.1.0$^{2,7}$]tridec-2,7-ene, disodium salt gave [4-(4-chlorophenoxy)-4-(3-phosphoryloxy-4-chlorophenyl)]spiro[1,2-dioxetane-3,13'-tricyclo[7.3.1.0$^{2,7}$]tridec-2,7-ene, disodium salt, correspond to the formula:

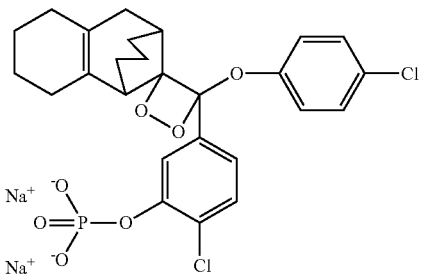

(104)

Example XV

This example illustrates the synthesis of [4-(2,4,6-Trichlorophenoxy)-4-(3-phosphoryloxy-4-chlorophenyl)]spiro[1,2-dioxetane-3,13'-tricyclo[7.3.1.0$^{2,7}$]tridec-2,7-ene, disodium salt:

This compound was synthesized by the following procedure:
By using 2,4,6-trichlorophenol as a starting material, the synthesis of [4-(2,4,6-Trichlorophenoxy)-4-(3-phosphoryloxy-4-chlorophenyl)]spiro[1,2-dioxetane-3,13'-tricyclo [7.3.1.0$^{2,7}$]tridec-2,7-ene, disodium salt was achieved by following steps (a) to (e) of Example XIV. The following structure was confirmed by NMR.

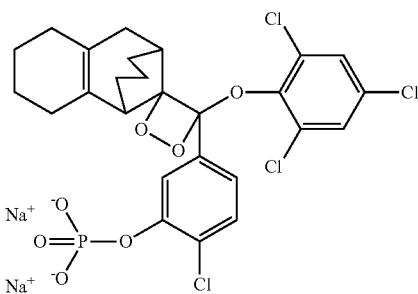

(105)

Example XVI

This example illustrates the synthesis of [4-Methoxy-4-(3-phosphoryloxy-4-cyanophenyl)]spiro[1,2 dioxetane-3,13'-tricycle[7.3.1.0$^{2,7}$]tridec-2,7-ene, disodium salt:

This compound was synthesized by the following procedure:

(a). Synthesis of Methyl 4-cyano-3-hydroxybenzoate

Into a 1000 ml round bottom flask 5 mL of concentrated sulfuric acid was added to a solution of 31.32 parts of 4-cyano-3-hydroxybenzoic acid in 500 mL of methanol and the solution was heated at reflux for 17 hrs. The reaction was monitored by TLC on silica gel plates showed formation of product. The solvent was evaporated under reduced pressure and residue was dissolved in 250 mL of ethyl acetate. The organic layer was washed with 2×100 mL of 5% aqueous sodium bicarbonate solution followed by 250 mL of deionized water. The organic solvent dried over anhydrous Na$_2$SO$_4$ and filtered. The solvent was evaporated under reduced pressure and the reaction mixture was purified by chromatography on silica gel with 25% ethyl acetate-hexanes. The product fractions (TLC) were combined and solvent was evaporated under reduced pressure to give off-white solid, yield 26.3 parts.

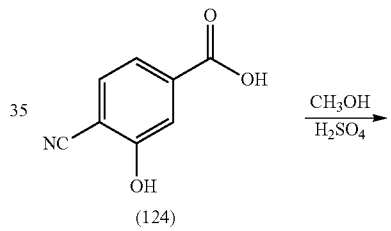

(124)

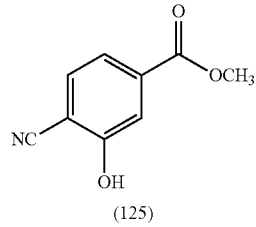

(125)

(b). Synthesis of methyl 4-cyano-3-silyloxybenzoate

Into a 500 mL round bottom flask 26 parts of methyl 4-cyano-3-hydroxybenzoate, 23.2 parts of tert-butyldimethylsilyl chloride and 23 parts of imidazole were dissolved in 35 mL of dry dimethylformamide and stirred at room temperature for 24 hrs. The reaction was monitored by TLC on a silica gel plate showed formation of product and diluted with 350 mL of deionized water. The product was extracted with 2×250 mL of hexanes. The organic layer was washed with 3×200 mL deionized water, dried over anhydrous Na$_2$SO$_4$ and filtered. The solvent was evaporated under reduced pressure and mixture was purified by chromatography on silica gel with 5% ethyl acetate-hexanes to give an oil, yield 42 parts.

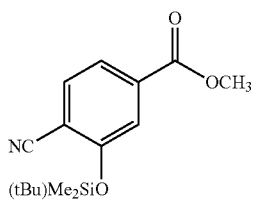

(109)

(c). Synthesis of (3-silyloxyoxy-4-cyanophenyl)methoxymethylene tricyclo[7.3.1.0$^{2,7}$]tridec-2,7-ene Into a 1 L three-neck flask equipped with mechanical stirrer, reflux condenser and pressure-equalizing addition funnel under nitrogen atmosphere was charged 100 mL of anhydrous tetrahydrofuran. Then 21.93 parts of TiCl$_4$ was added drop wise over 25 min and the suspension was stirred for 10 min. Now 18.44 parts of Zn dust was added carefully in small portions over 25 min to the suspension. The reaction mixture was heated at reflux for 4 hr 30 min and 53 mL of Et$_3$N was added drop wise over 10 minutes. After refluxing the reaction mixture for 1 hr, solution of 4.2 parts of methyl 4-cyano-3-silyloxybenzoate and 3.86 parts of ketone 18 in 250 mL anhydrous tetrahydrofuran was added drop wise over 2 hr 35 min. After 10 min a solution of 0.6 parts of ketone 19 in 5 mL tetrahydrofuran added over 30 min and refluxed for 6 hrs. The reaction mixture was cooled to room temperature and diluted with 150 mL of 1:1 mixture of ethyl acetate-hexanes. The mixture was filtered and the solid was washed with 3×25 mL 1:1 solvent mixture. The combined filtrate was evaporated under reduced pressure and mixture was purified by chromatography on silica gel with ethyl acetate-hexanes mixture containing 0.25% Et$_3$N. The product fractions (TLC) were combined and evaporated under reduced to oil, yield 4.95 parts of (3-silyloxyoxy-4-cyanophenyl)methoxymethylene tricyclo[7.3.1.0$^{2,7}$]tridec-2,7-ene.

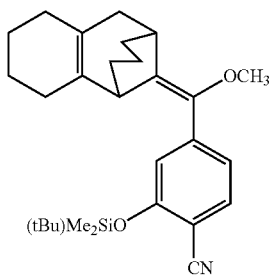

(109)

(d). Synthesis of (3-Hydroxy-4-cyanophenyl)methoxymethylene tricyclo[7.3.1.0$^{2,7}$]tridec-2,7-ene Into a 220 mL round bottom flask 3.81 parts of 75 wt. % solution of tetrabutylammonium fluoride in water was added over 15 min to a solution of 4.92 parts of (3-silyloxyoxy-4-cyanophenyl)methoxymethylene tricyclo[7.3.1.0$^{2,7}$]tridec-2,7-ene in 50 mL of tetrahydrofuran and stirred at room temperature for 2 hr. The reaction mixture was evaporated under reduced pressure and residue was extracted with 1 L of methylene chloride. The organic layer dried over anhydrous Na$_2$SO$_4$ and filtered. The solvent was evaporated under reduced pressure and residual mixture was purified by chromatography on silica gel with 25% ethyl acetate-hexanes containing 0.25% Et$_3$N. The product fractions (TLC) were combined and evaporated under reduced pressure to give an oil, yield 35.7 parts (3-Hydroxy-4-cyanophenyl)methoxymethylene tricyclo[7.3.1.0$^{2,7}$]tridec-2,7-ene.

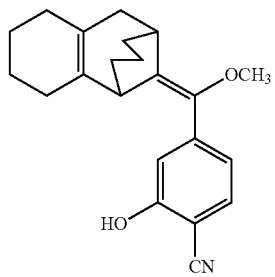

(110)

(e). Synthesis of (3-phosphoryloxy-4-cyanophenyl)methoxymethylene[7.3.1.0$^{2,7}$]tricyclo tridec-2,7-ene, disodium salt Into a 3 mL three-neck round bottom flask equipped with mechanical stirrer and pressure equalizing addition funnel under nitrogen atmosphere was added solution of 5.04 parts of phosphorous oxychloride in 300 mL of dichloromethane and cooled to 5° C. A solution of 3.56 parts of (3-Hydroxy-4-cyanophenyl)methoxymethylene tricyclo[7.3.1.0$^{2,7}$]tridec-2,7-ene and 9.09 parts of anhydrous pyridine in 25 mL of dichloromethane was added to the cold solution over 4 hrs. The reaction mixture was stirred at room temperature for 3 hrs. The reaction mixture cooled to 5° C. and a solution of 5.82 parts of 3-hydroxypropionitrile and 6.47 parts of anhydrous pyridine in 250 mL dichloromethane was added drop wise to the reaction mixture over 45 min. The reaction mixture was stirred for 48 hrs at room temperature and cooled to 5° C. for 1 hr 15 min. The mixture was filtered and washed with cold 25 mL dichloromethane. The solvent was evaporated under reduced pressure and mixture was purified by chromatography on silica gel with 75% ethyl acetate-hexane containing 0.25% Et$_3$N. The product fractions (TLC) were combined and the solvent was evaporated under reduced pressure gave pure phosphate ester as an oil, yield 2.46 parts. The phosphate ester was dissolved in 100 mL of acetone and 2.36 mL of 20% aqueous NaOH solution was added drop wise over 15 min. Stirring was continued for 2 hr and the mixture was diluted with 400 mL of acetonitrile. The solid was filtered and washed with 2×50 mL of acetone. The solid material was crystallized from a methanol and acetone mixture. The solid was filtered, washed with 2×25 mL acetone and dried to give 2.02 parts of (3-phosphoryloxy-4-cyanophenyl)methoxymethylene[7.3.1.0$^{2,7}$]tricyclo tridec-2,7-ene, disodium salt.

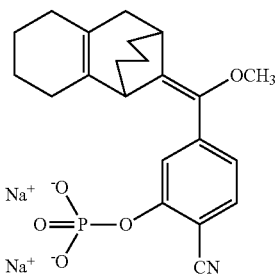

(111)

(f). Synthesis of [4-Methoxy-4-(3-phosphoryloxy-4-cyanophenyl)]spiro[1,2 dioxetane-3,13'-tricyclo[7.3.1.0$^{2,7}$]tridec-2,7-ene, disodium salt (123)

A solution of (3-phosphoryloxy-4-cyanophenyl) methoxymethylene[7.3.1.0$^{2,7}$]tricyclo tridec-2,7-ene, disodium salt in methanol and methylene chloride mixture was photo-oxidized as described above to give [(4-methoxy-4-(3-phosphoryloxy-4-cyanophenyl)]spiro[1,2-dioxetane-3,13'-tricycle[7.3.1.0$^{2,7}$]tridec-2,7-ene], disodium salt.

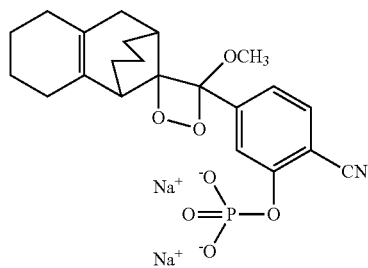

(112)

Example XVII

This example illustrates the synthesis of [(4-methoxy (D$_3$)-4-(3-phosphoryloxy-4-cyanophenyl)]spiro[1,2-dioxetane-3,2'-5-chloroadamantane], disodium salt:
This compound was synthesized by the following procedure:

(a). Synthesis of Methyl(D$_3$) 4-cyano-3-hydroxybenzoate

Into a 100 mL round bottom flask 0.5 mL of concentrated sulfuric acid was added to a solution of 3.1 parts of 4-cyano-3-hydroxybenzoic acid in 50 mL of CD$_3$OD and the solution was heated at reflux for 17 hrs. The reaction was monitored by TLC on silica gel plates showed formation of product. The solvent was evaporated under reduced pressure and residue was dissolved in 25 mL of ethyl acetate. The organic layer was washed with 2×100 mL of 5% aqueous sodium bicarbonate solution followed by 250 mL of deionized water. The organic solvent dried over anhydrous Na$_2$SO$_4$ and filtered. The solvent was evaporated under reduced pressure and the reaction mixture was purified by chromatography on silica gel with 25% ethyl acetate-hexanes. The product fractions (TLC) were combined and solvent was evaporated under reduced pressure to give off-white solid, yield 2.6 parts of the following structure.

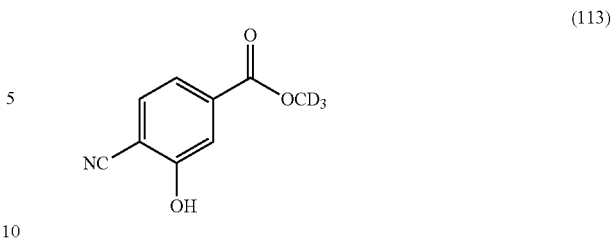

(113)

The synthesis of [(4-methoxy (D$_3$)-4-(3-phosphoryloxy-4-cyanophenyl)]spiro[1,2-dioxetane-3,2'-5-chloroadamantane], disodium salt was achieved by following steps (b) to (f) as described in Example XVI. In step (c) 5-chloro-2-adamantanone was used and other conditions were similar. The isolated yield was 3.02 parts of the following structure confirmed by NMR.

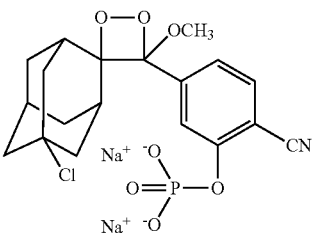

(114)

Example XVIII

This example illustrates the synthesis of [(4-methoxy (D$_3$)-4-(3-phosphoryloxy-4-cyanophenyl)]spiro[1,2-dioxetane-3,2'-5-methoxyadamantane], disodium salt:

This compound was synthesized by the following procedure:

(a) Synthesis of (3-hydroxy-4-cyanophenyl) methoxy (D$_3$) methylene-5-methoxyadamantane Into a 1 L three-neck flask equipped with mechanical stirrer, reflux condenser and pressure-equalizing addition funnel under nitrogen atmosphere was charged 250 mL of anhydrous tetrahydrofuran. Then 40.1 parts of TiCl$_4$ was added drop wise over 7 min and the suspension was stirred for 8 min. Now 36.3 parts of Zn dust was added carefully in small portions over 15 min to the suspension. The reaction mixture was heated at reflux for 4 hr 30 min and 108 mL of Et$_3$N was added drop wise over 10 minutes. After refluxing the reaction mixture for 1 hr, a solution of 8.2 parts of Methyl(D$_3$) 4-cyano-3-hydroxybenzoate and 5.03 parts of 5-methoxy-2-adamantanone in 125 mL anhydrous tetrahydrofuran was added drop wise over 75 min and refluxed for 6 hrs. The mixture was cooled to room temperature and diluted with 500 mL ethyl acetate. The mixture was filtered and the solid was washed with 2×100 mL ethyl acetate. The combined filtrate was evaporated under reduced pressure and the mixture was purified by chromatography on silica gel with 10% ethyl acetate-hexanes containing 0.25% Et$_3$N. The product fractions (TLC) were combined and evaporated under reduced to give an oil, yield 10.5 parts of the following alkene structure confirmed by NMR.

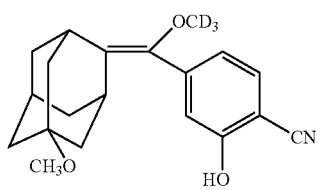
(115)

(b). Synthesis of (3-phosphoryloxy-4-cyanophenyl)methoxy ($D_3$) methylene-5-methoxyadamantane, disodium salt was achieved, as described in Example XVI step (e) to give 5.6 parts of the following structure confirmed by NMR.

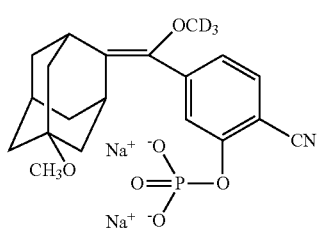
(116)

(c). Synthesis of [(4-methoxy ($D_3$)-4-(3-phosphoryloxy-4-cyanophenyl)]spiro[1,2-dioxetane-3,2'-5-methoxyadamantane], disodium salt The disodium phosphate salt of (3-phosphoryloxy-4-cyanophenyl)methoxy ($D_3$) methylene-5-methoxyadamantane was photo-oxidized as described above to give [(4-methoxy ($D_3$)-4-(3-phosphoryloxy-4-cyanophenyl)]spiro[1,2-dioxetane-3,2'-5-methoxyadamantane], disodium salt:

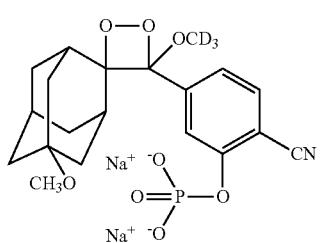
(117)

Example XIX

This example illustrates the synthesis of [(4-methoxy (D3)-4-(3-phosphoryloxy-4-cyanophenyl)]spiro[1,2-dioxetane-3,13'-tricycle[7.3.1.0$^{2,7}$]tridec-2,7-ene, disodium salt:
This compound was synthesized by the following procedure:

(a). Synthesis of (3-hydroxy-4-cyanophenyl) methoxy ($D_3$) methylene tricyclo[7.3.1.0$^{2,7}$]tridec-2,7-ene A similar procedure was used by using 10.28 parts of the methyl($D_3$)-3hydroxy-4-cyanobenzoate and 7.5 parts of tricyclo[7.3.1.0$^{2,7}$]tridec-2,7-ene-13-one as described in Example XVIII step (a) to give an oil, 6.2 parts of the following structure confirmed by NMR.

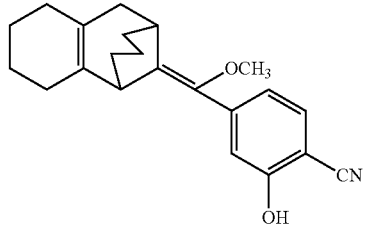
(118)

(b) Synthesis of (3-phosphoryloxy-4-cyanophenyl)methoxy ($D_3$) methylene tricyclo[7.3.1.0$^{2,7}$]tridec-2,7-ene, disodium salt was achieved as described in Example XVI step (e) using 6.2 parts of (3-hydroxy-4-cyanophenyl) methoxy ($D_3$) methylene tricyclo[7.3.1.0$^{2,7}$]tridec-2,7-ene to give 3.8 parts of the following structure confirmed by NMR.

(119)

(c). Synthesis of [(4-methoxy (D3)-4-(3-phosphoryloxy-4-cyanophenyl)]spiro[1,2-dioxetane-3,13'-tricyclo[7.3.1.0$^{2,7}$]tridec-2,7-ene, disodium salt Disodium phosphate salt, 3.8 parts, of (3-phosphoryloxy-4-cyanophenyl) methoxy ($D_3$) methylene tricyclo[7.3.1.0$^{2,7}$]tridec-2,7-ene was photo-oxidized as reported above to give [(4-methoxy (D3)-4-(3-phosphoryloxy-4-cyanophenyl)]spiro[1,2-dioxetane-3,13'-tricyclo[7.3.1.0$^{2,7}$]tridec-2,7-ene, disodium salt.

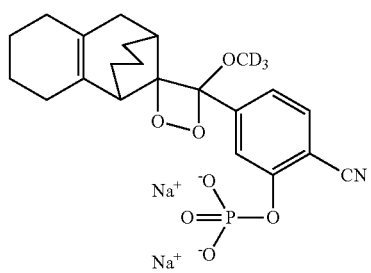
(120)

Example XX

This example illustrates the synthesis of bis{[(4-methylenoxy)-4-(3-phosphoryloxyphenyl)]spiro[1,2-dioxetane-3,2'-adamantane], disodium salt};
This compound was synthesized by the following procedure:

(a). Synthesis of tert-Butyldimethylsilyl 3-tertbutyldimethylsilyloxybenzoate Into a 500 mL round bottom flask 13.95 parts of 3-hydroxy benzoic acid, 33.5 parts of tert-butyldimethylsilyl chloride and 31.3 parts of imidazole were dissolved in 31 mL of dry dimethylformamide and stirred at room temperature for 22 hrs. The reaction mixture was diluted with 300 mL of deionized water and the product was extracted with 2×250 mL of hexanes. The hexanes layer was washed with 3×200 mL deionized water, dried over anhydrous $Na_2SO_4$ and filtered. The solvent was evaporated under reduced pressure to give an oil, yield 37.6 parts of the following structure confirmed by NMR.

(121)

(b). Synthesis of 3-tert-Butyldimethylsilyloxybenzoic acid

Into a 500 mL round bottom flask 38 mL of 5% aqueous NaOH solution was added over 5 min to a solution of 37.6 parts of tert-butyldimethylsilyl 3-tert-butyldimethylsilyloxy benzoate in 185 mL of tetrahydrofuran and the reaction mixture was stirred for 10 min at room temperature. The reaction was monitored by TLC on a silica gel plate showed formation of product. The reaction mixture was concentrated under reduced pressure and purified by column chromatography on silica gel with 30% ethyl acetate-hexane to yield 20.3 parts of an oily product having the following structure confirmed by NMR.

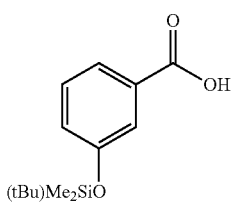

(122)

(c). Synthesis of 3-tert-Butyldimethylsilyloxybenzoyl chloride

Into a 100 mL round bottom flask a mixture of 5 parts of 3-tert-butyldimethylsilyloxybenzoic acid and 25 mL of thionyl chloride was heated at reflux for 90 mins. The reaction mixture was concentrated under reduced pressure to give an oil, yield 5.77 parts of the following structure.

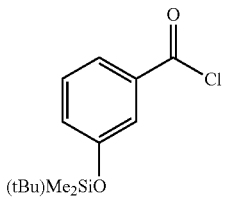

(123)

(d). Synthesis of bis[methylenoxy 3-tert-butyldimethylsilyloxy benzoate]

Into a 100 ml three neck round bottom flask equipped with magnetic stirrer and pressure-equalizing addition funnel under an argon blanket was charged a solution containing 0.617 parts of ethylene glycol and 2.38 parts of pyridine in 10 mL dichloromethane and cooled to 5° C. A solution of 5.77 parts of 3-tert-butyldimethylsilyloxybenzoyl chloride in 25 mL of dichloromethane was added drop wise over 20 min to a cold solution and stirred for additional 30 mins. The reaction mixture was stirred at room temperature for 20 hrs. The reaction was monitored by TLC on silica gel plate showed formation of product. The reaction mixture was diluted with 50 mL of dichloromethane and washed with 3×50 mL of deionized water. The organic layer was separated, dried over anhydrous $Na_2SO_4$ and filtered. The solvent was evaporated under reduced pressure and mixture was purified by chromatography on silica gel with 5% ethylacetate-hexane. The product fractions (TLC) were combined and evaporated under reduced pressure to give an oil, yield 2.9 parts of the following structure confirmed by NMR.

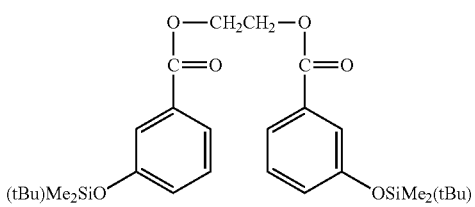

(124)

(e). Synthesis of bis-[(3-tert-butyldimethylsilyloxyphenyl)methylenoxymethylene adamantane]

Into a 2 L three-neck flask equipped with mechanical stirrer, reflux condenser and pressure-equalizing addition funnel under nitrogen atmosphere was charged 200 mL of anhydrous tetrahydrofuran. 44.2 parts of $TiCl_4$ was added drop wise over 10 min and the suspension was stirred for 5 min. Then 36.4 parts of Zn dust was added carefully in small portions over 20 min to the suspension. The reaction mixture was heated at reflux for 4 hrs and 115 mL of $Et_3N$ was added over 10 min. After refluxing the mixture for 1 hr, a solution of 5.27 parts of bis[methylenoxy 3-tert-butyldimethylsilyloxy benzoate] and 3.52 parts of 2-adamantanone in 100 mL anhydrous tetrahydrofuran was added drop wise over 1 hr. After 10 min additional 0.8 parts of 2-admantanone in 20 mL anhydrous tetrahydrofuran was added drop wise over 30 min. After refluxing for 6 hrs, the mixture was cooled to room temperature and diluted with 400 mL of 1:1 mixture of ethyl acetate-hexanes. The mixture was filtered and the solid was washed with 3×125 mL 1:1 mixture. The combined filtrate was evaporated under reduced pressure and mixture was purified by chromatography on silica gel with hexanes-ethyl acetate mixtures containing 0.25% Et$_3$N. The product fractions (TLC) were combined and evaporated under reduced pressure to give an oil, yield 6.84 parts of the following structure confirmed by NMR.

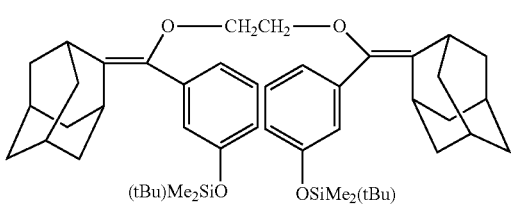

(125)

(f). Synthesis of bis[(3-hydroxyphenyl)methylenoxymethylene adamantane]

Into a 250 mL round bottom flask 6.82 parts of 75 wt. % solution of tetrabutylammonium fluoride in water was added over 10 min to a solution of 6.63 parts of bis-[(3-tert-butyldimethylsilyloxyphenyl)methylenoxymethylene adamantane] in 65 mL of tetrahydrofuran and stirred at room temperature for 2 hr. The reaction was monitored by TLC on a silica gel plate showed formation of product. Solvent was evaporated under reduced pressure and residue was extracted with 150 mL dichloromethane. The organic layer was separated, dried over anhydrous Na$_2$SO$_4$ and filtered. The solvent was evaporated under reduced pressure and solid was purified by chromatography on silica gel with ethyl acetate-hexanes mixtures. The product fractions (TLC) were combined and evaporated under reduced pressure to give white solid, yield 4.87 parts of the following structure confirmed by NMR.

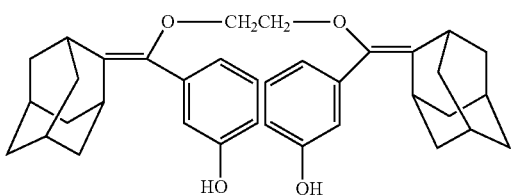

(126)

(g). Synthesis of bis[(3-phosphoryloxyphenyl)methylenoxymethylene adamantane, disodium salt]

Into a 1 L three-neck round bottom flask equipped with magnetic stirrer and pressure-equalizing addition funnel under nitrogen atmosphere was added solution of 8.13 parts of phosphorous oxychloride in 50 mL of dichloromethane and cooled to 5° C. A solution of 4.72 parts of bis[(3-hydroxyphenyl)methylenoxymethylene adamantine] and 14.61 parts of anhydrous pyridine in 100 mL of dichloromethane was added to the cold solution over 2 hrs. The reaction mixture was stirred at room temperature for 3 hrs. The reaction was monitored by TLC on a silica gel plate showed formation of product. The reaction mixture cooled to 5° C. and a solution of 9.35 parts of 3-hydroxypropionitrile and 10.4 parts of anhydrous pyridine in 50 mL dichloromethane was added drop wise to the reaction mixture over 30 mins. The reaction mixture was stirred for 16 hrs at room temperature and was cooled to 5° C. for 30 min and the solid was filtered and washed with cold 15 mL dichloromethane. The solvent was evaporated under reduced pressure and mixture was purified by chromatography on silica gel with 75% ethyl acetate-hexane containing 0.25% Et$_3$N. The product fractions (TLC) were combined and the solvent was evaporated under reduced pressure to give an oil, yield 5.13 parts. The phosphate ester was dissolved in 250 ml of acetone and 5.2 mL of 10% aqueous NaOH solution was added drop wise over 10 min. Stirring was continued for 2 hrs and the mixture was diluted with 25 mL of acetonitrile. The solid was filtered and washed with 5 mL of acetone. The solid was crystallized from methanol and acetone mixture. The solid was filtered, washed with 5 mL acetone and dried to yield 4.3 parts of the following structure confirmed by NMR.

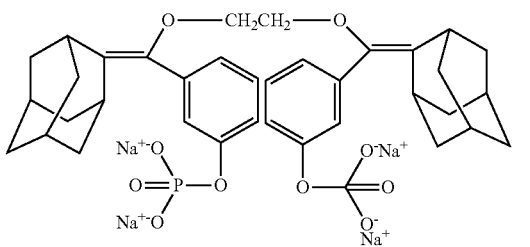

(127)

(h). Synthesis of Bis{[(4-methylenoxy)-4-(3-phosphoryloxyphenyl)]spiro[1,2-dioxetane-3,2'-adamantane], disodium salt} (146)

The disodium phosphate salt of bis[(3-phosphoryloxyphenyl)methylenoxymethylene adamantine] was photo-oxidized as described above gave bis{[(4-methylenoxy)-4-(3-phosphoryloxyphenyl)]spiro[1,2-dioxetane-3,2'-adamantane], disodium salt} of the following structure confirmed by NMR.

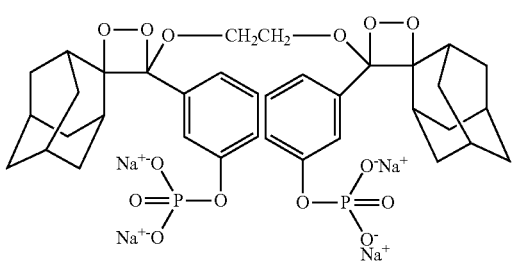

(128)

Example XXI

This example illustrates the synthesis of bis-{[(4-methylenoxy)-4-(3-phosphoryloxy-4-cholorophenyl)]spiro[1,2-dioxetane-3,2'-adamantane], disodium salt}:

This compound was synthesized by following the procedure of steps (a) to (h) of Example XX but therein 3-hydroxy-4chlorobenzoic acid was as the starting acid. The following structure of the product was assigned by NMR.

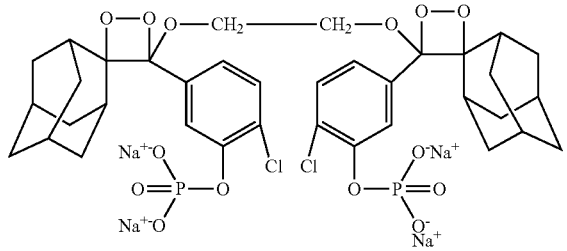

(129)

Example XXII

This example illustrates the synthesis of bis-{[(4-methoxy)-4-(3-phosphoryloxy-4-cholorophenyl)]spiro[1,2-dioxetane-3,2'-5-chloroadamantane], disodium salt}:

This compound was synthesized by following the procedure of steps (a) to (h) of Example XX but using 3-hydroxy-4-chlorobenzoic acid in place of 3-hydroxybenzoic acid and in step (e) using 5-chloro-2-adamantanone as the reactant in place of 2-adamantanone. The following structure of the product was assigned by NMR.

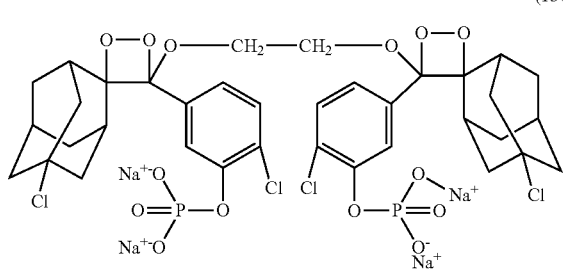

(130)

Example XXIII

Synthesis of bis{[(4-methoxy)-4-(3-phosphoryloxy-4-chlorophenyl)]spiro[1,2-dioxetane-3,13'-tricyclo [7.3.1.0$^{2,7}$]tridec-2,7-ene], disodium salt} (165)

This compound was synthesized using the procedure of steps (a) to (h) of Example XX but using 3-hydroxy-4chlorobenzoic acid in place of 3-hydroxybenzoic acid and tricyclo[7.3.1.0$^{2,7}$]tridec-2,7-ene-13-one (18) was the reactant in place of 2-adamantanone. The following structure of the product was assigned by NMR.

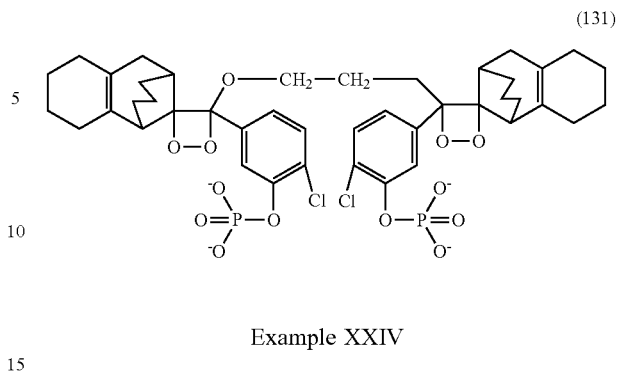

(131)

Example XXIV

Synthesis of bis[{(4-methoxy(D3)-4-(3-phosphoryloxy-4-chlorophenyl)}spiro {1,2-dioxetane-3,2'-(5-oxy-adamantane)}, disodium salt] methane This compound was synthesized by the following procedure:

(a). Synthesis of bis-[5-oxy-adamantan-2-one]methane

Into 1 L three neck flask equipped with magnetic stirrer, pressure-equalizing addition funnel and reflux condensor under nitrogen atmosphere, 12.7 parts of sodium hydride (60% dispersion in mineral oil) was mixed with 125 mL of hexane and stirred for 3 mins. Stirring was stopped for 5 min and hexane decanted off. This process was repeated with additional 2×125 mL hexane and suspended in 125 mL of anhydrous tetrahydrofuran. Then 43 parts of 5-hydroxy-2-adamantanone was added portion wise over 2 min and the reaction mixture was heated at reflux for 90 mins. After the reaction mixture was cooled to room temperature and 62 parts of chloroiodomethane was added at once and the reaction mixture was heated at reflux for 22 hrs. The reaction mixture was cooled to 30° C. and 23.8 parts chloroiodomethane was added at once and heated at reflux for 48 hrs. The solution was cooled to room temperature and concentrated under reduced pressure and residue was extracted with 350 mL of dichloromethane. The organic layer was dried over anhydrous Na$_2$SO$_4$ and filtered. The solvent was evaporated under reduced pressure and the mixture was purified by chromatography on silica gel with 20% ethyl acetate-hexanes. The product fractions (TLC) were combined and solvent was evaporated under reduced pressure to give 12.72 parts of a white solid of the following structure confirmed by NMR.

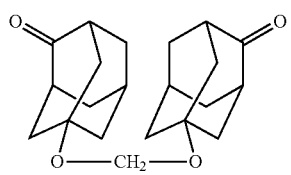

(132)

(b). Synthesis of bis[(3-hydroxy-4-chlorophenyl) methoxy(D3)methylene5-oxy-adamantane]methane Into a 2 L three-neck flask equipped with mechanical stirrer, reflux condenser and pressure-equalizing addition funnel under nitrogen atmosphere was charged 250 mL of anhydrous tetrahydrofuran. 45.9 parts of TiCl₄ was added drop wise over 10 min and the suspension was stirred for 10 min. Then 40.3 parts of Zn dust was added carefully in small portions over 15 min to the suspension. The reaction mixture was heated at reflux for 4 hrs and 30 mins and 115 mL of Et₃N was added drop wise over 10 minutes. After refluxing the mixture for 45 mins, solution of 7.85 parts of methyl 4-chloro-3-hydroxybenzoate and 4.1 parts of bis-[5-oxy-adamantan-2-one]methane in 125 mL anhydrous tetrahydrofuran was added drop wise over 2 hrs and refluxed for 6 hrs. The mixture was cooled to room temperature and diluted with 500 mL of ethyl acetate. The reaction mixture was filtered and the solid was washed with ethyl acetate. The combined filtrate was evaporated under reduced pressure and the mixture was purified by chromatography on silica gel with ethyl acetate-hexanes mixture containing 0.25% Et₃N. The product fractions (TLC) were combined and evaporated under reduced pressure to give an oil, yield 2.94 parts of the following structure confirmed by NMR.

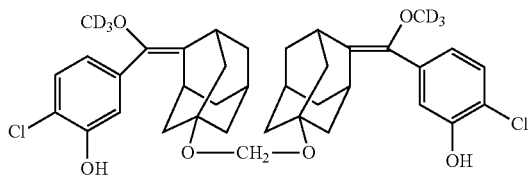

(133)

(c). Synthesis of bis-[(3-phosphoryloxy-4-chlorophenyl)methoxy(D3)methylene-5-oxy-adamantane, disodium salt] methane Into a 500 mL three-neck round bottom flask equipped with magnetic stirrer and pressure equalizing addition funnel under nitrogen atmosphere was added solution of 2.86 parts of phosphorous oxychloride in 30 mL of dichloromethane and cooled to 5° C. A solution of 2.04 parts of bis-[(3-hydroxy-4-chlorophenyl)methoxy(D3)methylene5-oxy-adamantane]methane and 5.15 parts of anhydrous pyridine in 45 mL of dichloromethane was added to the cold solution over 2 hrs. The reaction mixture was stirred at room temperature for 3 hr. The reaction was monitored by TLC on a silica gel plate showed formation of product. The reaction mixture cooled to 5° C. (ice-water) and a solution of 3.31 parts of 3-hydroxypropionitrile and 3.7 parts of anhydrous pyridine in 30 mL dichloromethane was added drop wise to the reaction mixture over 35 mins. The reaction mixture was stirred for 26 hrs at room temperature and was cooled to 5° C. for 45 mins and the solid was filtered and washed with cold 15 mL dichloromethane. The filtrate was evaporated under reduced pressure and mixture was purified by chromatography on silica gel with 75% ethyl acetate-hexane containing 0.25% Et₃N. The product fractions (TLC) were combined and the solvent was evaporated under reduced pressure give phosphate ester as an oil, yield 1.54 parts. The phosphate ester was dissolved in 40 ml of acetone and 3 mL of 10% aqueous NaOH solution was added at once. Stirring was continued for 2 hr and the mixture was diluted with 15 mL of acetonitrile. The solid was filtered and washed with 2 mL of acetone. The solid material was crystallized from a methanol and acetone mixture. The solid was filtered, washed with 2 mL of acetone and dried to yield 1.28 parts of the following compound confirmed by NMR.

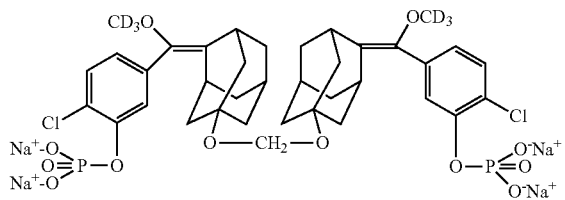

(134)

Photooxidation of bis[(3-phosphoryloxy-4-chlorophenyl)methoxy(D3)methylene5-oxy-adamantane, disodium salt] methane The disodium phosphate salt of bis-[(3-phosphoryloxy-4-chlorophenyl)methoxy(D3)methylene-5-oxy-adamantane] methane was photooxidized as described above to give bis[{(4-methoxy(D3)-4-(3-phosphoryloxy-4-chlorophenyl)}spiro{1,2-dioxetane-3,2'-(5-oxy-adamantane)}, disodium salt] methane of the following structure confirmed by NMR.

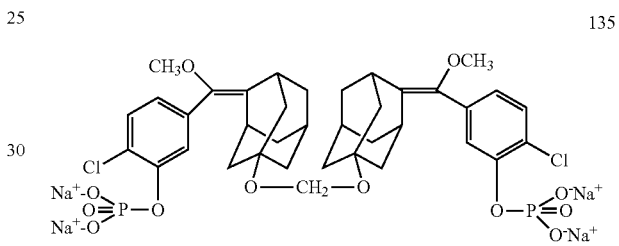

135

Example XXV

Synthesis of bis[{(4-methoxy(D3)-4-(3-phosphoryloxy-4-cyanophenyl)}spiro {1,2-dioxetane-3,2'-(5-oxy-adamantane)}, disodium salt] methane This compound was synthesized using the following procedure of steps (a) to (d) of example XXIV but in step (b) methyl3-hydroxy-4cyanobenzoate was used in place of methyl(D3)₃-hydroxy-4-chloroobenzoate. The following structure for the product was assigned by NMR.

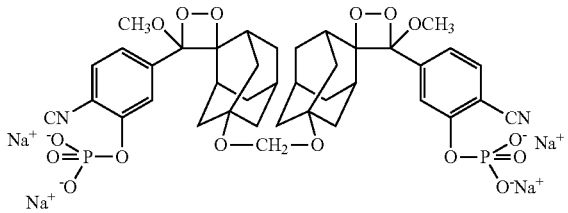

(136)

Example XXVI

Synthesis of bis[{(4-methoxy-4-(3-phosphoryloxyphenyl)}spiro{1,2-dioxetane-3,2'-(5-oxy-adamantane)}, disodium salt] methane This compound was synthesized following the procedure of steps (a) to (d) as described in Example XXIV but in step (b)

methyl3-hydroxybenzoate was used in place of methyl(D3) 3-hydroxy-4-chloroobenzoate. The following structure of the product was assigned by NMR.

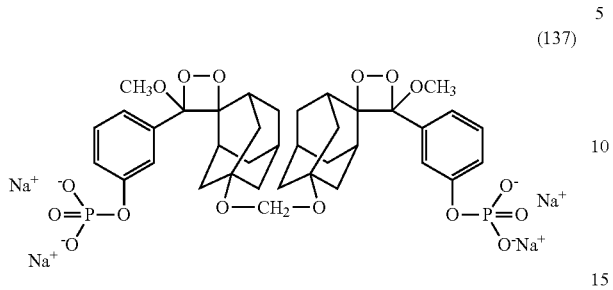

(137)

Example XXVII

Synthesis of [4-methoxy($D_3$)-4-(3-β-D-galactose-4-chlorophenyl)]spiro[1,2-dioxetane-3,2'-adamantane This compound was synthesized by the following procedure:

Synthesis of [(3-β-D-galactose-4-chlorophenyl)-(2-methoxy ($D_3$) methylene]adamantane Into a 250 mL round bottom flask 15 mL aqueous sodium hydroxide solution (15 parts of sodium hydroxide in 15 mL of deionized water) was added to a solution of 10.1 parts of [(3-Hydroxy-4-chlorophenyl)-2-methoxy ($D_3$) methylene] adamantane in 75 mL of acetone at room temperature with vigorous stirring and stirred for 10 min. Then 17 parts of acetobromo-α-D-galactose was added portion wise over 20 mins to mixture and stirred vigorously for 23 hrs. The reaction mixture was concentrated under reduced pressure and the reaction mixture was extracted with 300 mL of dichloromethane. The organic layer was dried over anhydrous $Na_2SO_4$ and filtered. The solution was concentrated under reduced pressure and crude mixture was purified by column chromatography over silica gel with 10% methanol-ethyl to yield 7.09 parts of the following compound confirmed by NMR.

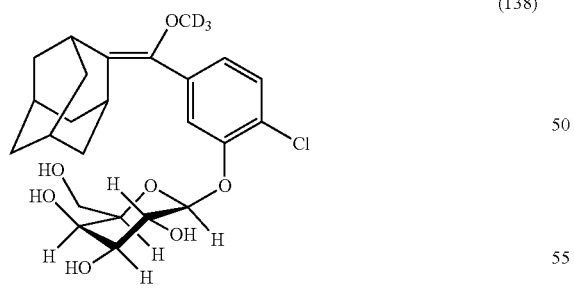

(138)

Synthesis of [4-methoxy($D_3$)-4-(3-β-D-galactose-4-chlorophenyl)]spiro[1,2-dioxetane-3,2'-adamantane A solution of [(3-β-D-galactose-4-chlorophenyl)-(2-methoxy ($D_3$) methylene]adamantine, 7.09 parts, in 270 mL of 1:1 mixture of dichloromethane-acetone was photooxidized as described above to give [4-methoxy($D_3$)-4-(3-β-D-galactose-4-chlorophenyl)]spiro[1,2-dioxetane-3,2'-adamantane.

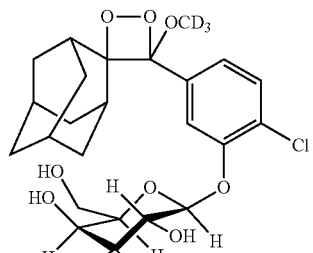

(139)

Example XXVIII

Synthesis of [(4-methoxy-4(3-β-D-galactose-4-cyanophenyl)]spiro[1,2-dioxetane-3-1,3-tricyclo [7.3.1.0$^{2,7}$]tridec-2,7-ene This compound was synthesized by the following procedure:

Synthesis of (3-β-D-galactose-4-cyanophenyl)methoxy methylene tricyclo[7.3.1.0$^{2,7}$]tridec-2,7-ene Into a 250 mL round bottom flask 16 mL aqueous sodium hydroxide solution (16 parts of sodium hydroxide in 16 mL of deionized water) was added to a solution of 11.35 parts of (3-hydroxy-4-cyanophenyl)methoxymethylene tricyclo [7.3.1.0$^{2,7}$]tridec-2,7-ene in 125 mL of acetone at room temperature with vigorous stirring and stirred for 15 min. Then 15.35 parts of acetobromo-α-D-galactose was added portion wise over 10 min to mixture and stirred vigorously for 20 hrs. The reaction mixture was concentrated under reduced pressure and residue was extracted with 300 mL of dichloromethane. The organic layer was dried over anhydrous $Na_2SO_4$ and filtered. The solution was concentrated under reduced pressure and mixture was purified by column chromatography over silica gel with 5% methanol-ethyl acetate gave to yield 10.8 parts of the following structure confirmed by NMR.

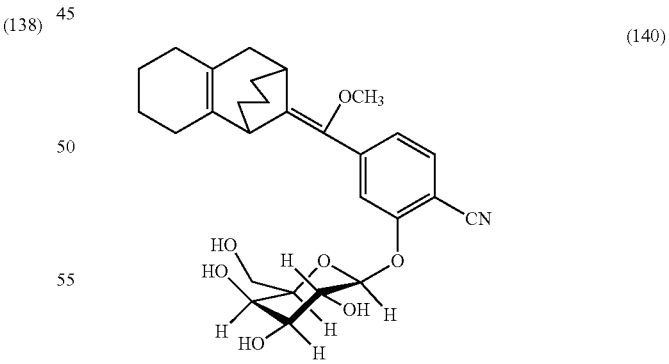

(140)

Synthesis of [(4-Methoxy-4(3-β-D-galactose-4-cyanophenyl)]spiro[1,2-dioxetane-3-1,3-tricyclo [7.3.1.0$^{2,7}$]tridec-2,7-ene (55)

A solution of, 10.6 parts, [(3-β-D-galactose-4-chlorophenyl)-(2-methoxy ($D_3$) methylene]adamantinein 270 mL of 1:1 mixture of dichloromethane-acetone was photo-oxidized as described above to give [4-methoxy(D₃)-4-(3-β-D-galactose-4-chlorophenyl)]spiro[1,2-dioxetane-3,2'-adamantane].

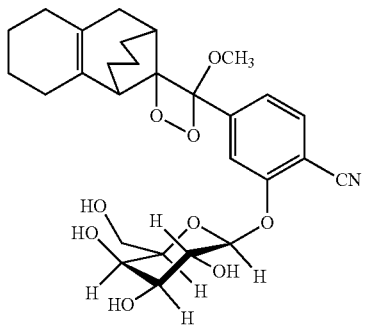

(141)

Example XXIX

Synthesis of [(4-methoxy(D₃)-4-(3-β-D-glucoside-4-chlorophenyl)]spiro[1,2-dioxetane-3,2'-adamantane]

This compound was synthesized by the following procedure:

Synthesis of [(3-β-D-glucoside-4-chlorophenyl)-(2-methoxy (D₃) methylene]adamantine Into a 250 mL round bottom flask 10 mL of aqueous sodium hydroxide solution (10.78 parts of sodium hydroxide in 10 mL of deionized water) was added to a solution of 7.75 parts of [(3-Hydroxy-4-chlorophenyl)-(2-methoxy (D₃) methylene]adamantane in 50 mL of acetone at room temperature with vigorous stirring and stirred for 10 min. Then 10 parts of 2,3,4,6-Tetra-O-acetyl-α-D-glucopyranosyl bromide added portion wise over 12 min and stirred vigorously for 20 hr. The reaction mixture was concentrated under reduced pressure and the reaction mixture was extracted with 400 mL of dichloromethane. The organic layer was dried over anhydrous Na₂SO₄ and filtered. The solution was concentrated under reduced pressure and mixture was purified by column chromatography over silica gel with 10% methanol-ethyl acetate to yield 4.95 parts of the following compound confirmed by NMR.

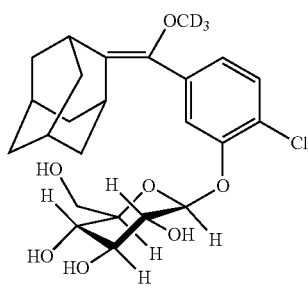

(142)

Synthesis of [(4-Methoxy(D₃)-4-(3-b-D-glucoside-4-chlorophenyl)]spiro[1,2-dioxetane-3,2'-adamantane]

A solution of, 4.95 parts, [(3-β-D-glucoside-4-chlorophenyl)-(2-methoxy (D₃) methylene]adamantinein 250 mL of 1:1 mixture of dichloromethane-acetone was photo-oxidized as described above to give [(4-Methoxy(D₃)-4-(3-b-D-glucoside-4-chlorophenyl)]spiro[1,2-dioxetane-3,2'-adamantane].

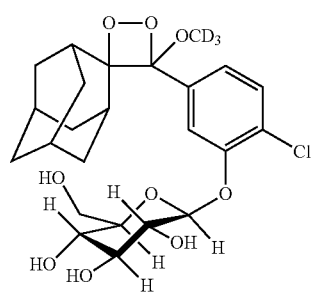

(143)

Example XXX

Synthesis of [(4-methoxy-4(3-β-D-glucoside-4-cyanophenyl)]spiro[1,2-dioxetane-3-1,3-tricyclo [7.3.1.0²,⁷]tridec-2,7-ene This compound was synthesized by the following procedure.

Synthesis of [(3-β-D-glucoside-4-cyanophenyl) methoxymethylene tricyclo[7.3.1.0²,⁷]tridec-2,7-ene Into a 250 mL round bottom flask 10 mL of aqueous sodium hydroxide solution (10.3 parts of sodium hydroxide in 10 mL of deionized water) was added to a solution of 7.3 parts of (3-hydroxy-4-cyanophenyl)methoxymethylene tricyclo[7.3.1.0²,⁷]tridec-2,7-ene (128) in 50 mL of acetone at room temperature with vigorous stirring and stirred for 10 min. Then 10 parts of 2,3,4,6-Tetra-O-acetyl-α-D-glucopyranosyl bromide added portion-wise over 8 min and stirred vigorously for 20 hrs. The reaction mixture concentrated under reduced pressure and extracted with 300 mL of dichloromethane. The organic layer was dried over anhydrous Na₂SO₄ and filtered. The solution was concentrated under reduced pressure and mixture was purified by column chromatography over silica gel with 5% methanol-ethyl acetate to yield 4.9 parts of the following compound confirmed by NMR.

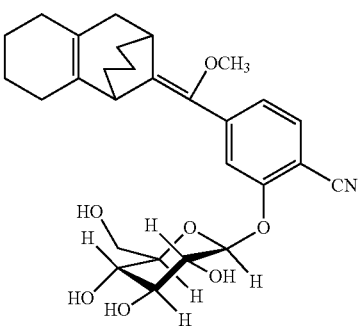

(144)

Synthesis of [(4-methoxy-4(3-β-D-glucoside-4-cyanophenyl)]spiro[1,2-dioxetane-3-1,3-tricyclo [7.3.1.0$^{2,7}$]tridec-2,7-ene A solution of, 4.9 parts, [(3-β-D-glucoside-4-cyanophenyl)methoxymethylene tricyclo[7.3.1.0$^{2,7}$]tridec-2,7-enein 240 mL of 1:1 mixture of dichloromethane-acetone was photo-oxidized as described above to give of [(4-methoxy-4(3-β-D-glucoside-4-cyanophenyl)]spiro[1,2-dioxetane-3-1,3-tricyclo[7.3.1.0$^{2,7}$]tridec-2,7-ene.

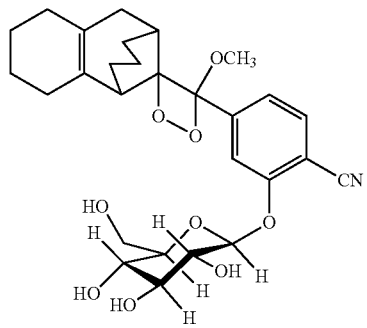

(145)

Example XXXI

Synthesis of Sodium [(4-methoxy (D$_3$)-4-(3-β-D-glucoronic acid-4-chlorophenyl)]spiro[1,2-dioxetane-3,2'-adamantane]

This compound was synthesized by the following procedure.

Synthesis of ethyl [(3-β-D-glucoronic acid-4-chlorophenyl)-2-methoxy (D$_3$) methylene]adamantine Into a 250 mL round bottom flask an aqueous sodium hydroxide solution (1.2 parts of sodium hydroxide in 1 mL of deionized water) was added to a solution of 3.7 parts of [(3-Hydroxy-4-chlorophenyl)-2-methoxy (D$_3$) methylene] adamantane in 100 mL of acetone maintained at room temperature with vigorous stirring and stirred for 30 min. The mixture was concentrated under reduced pressure and the solid was dried under vacuum for 1 hr. The solid was dissolved in 45 mL of anhydrous ethanol and 5 parts of acetobromo-α-D-glucoronic acid methyl ester added quickly to the solution. The dark brown solution was stirred for 4 hr 30 min at room temperature. The reaction mixture was concentrated under reduced pressure and extracted with 250 mL of dichloromethane. The organic layer was dried over anhydrous Na$_2$SO$_4$ and filtered. The solution was concentrated under reduced pressure and mixture was purified by column chromatography over silica gel with 80% ethyl acetate-hexanes to yield 1.55 parts of the following compound confirmed by NMR.

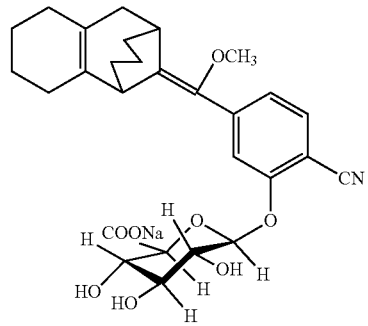

(146)

Synthesis of Sodium [(4-methoxy(D$_3$)-4-(3-β-D-glucoronic acid-4-chlorophenyl)spiro[1,2-dioxetane-3,2'-adamantane]

A solution of, 1.55 parts, ethyl [(3-β-D-glucoronic acid-4-chlorophenyl)-2-methoxy (D$_3$) methylene]adamantane in 50 mL of 1:1 mixture of dichloromethane-acetone was photo-oxidized as described above to give Sodium [(4-methoxy(D$_3$)-4-(3-β-D-glucoronic acid-4-chlorophenyl)] spiro[1,2-dioxetane-3,2'-adamantane].

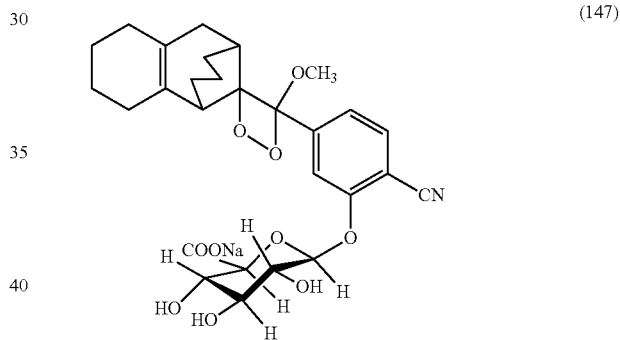

(147)

Example XXXII

Synthesis of Sodium [(4-methoxy-4(3-β-D-glucoronic acid-4-cyanophenyl)]spiro[1,2-dioxetane-3-1,3-tricyclo[7.3.1.0$^{2,7}$]tridec-2,7-ene This compound was synthesized by the following procedure.

Synthesis of ethyl[(3-β-D-glucoronic acid)-4-cyanophenyl]methoxymethylene tricyclo[7.3.1.0$^{2,7}$]tridec-2,7-ene Into a 250 mL round bottom flask an aqueous sodium hydroxide solution (1.03 parts of sodium hydroxide in 1 mL of deionized water) was added to a solution of 4.2 parts of 3-hydroxy-4-cyanophenyl)methoxymethylene tricyclo [7.3.1.0$^{2,7}$]tridec-2,7-ene (128) in 100 mL of acetone at room temperature with vigorous stirring and stirred for 30 min. The mixture was concentrated under reduced pressure and the solid was dried under vacuum for 35 min. The solid was dissolved in 60 mL of anhydrous ethanol and 5 parts of acetobromo-α-D-glucoronic acid, methyl ester added quickly to the solution. The dark brown solution was stirred for 6 hrs at room temperature, concentrated under reduce pressure and extracted 200 mL of dichloromethane. The organic layer was dried over anhydrous $Na_2SO_4$ and filtered. The solution was concentrated under reduced pressure and mixture was purified by column chromatography over silica gel with 80% ethyl acetate-hexanes to yield 1.3 parts of the following structure confirmed by NMR.

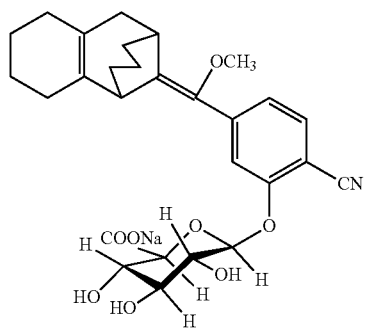

(148)

Synthesis of sodium [(4-methoxy-4(3-β-D-glucuronic acid-4-cyanophenyl)]spiro[1,2-dioxetane-3-1,3-tricyclo[7.3.1.0$^{2,7}$]tridec-2,7-ene A solution of, 1.3 parts, ethyl[(3-β-D-glucuronic acid)-4-cyanophenyl]methoxymethylene tricyclo[7.3.1.0$^{2,7}$]tridec-2,7-ene in 75 mL of 1:1 mixture of dichloromethane-acetone was photo-oxidized as described above to give sodium [(4-methoxy-4(3-β-D-glucuronic acid-4-cyanophenyl)]spiro[1,2-dioxetane-3-1,3-tricyclo[7.3.1.0$^{2,7}$]tridec-2,7-ene.

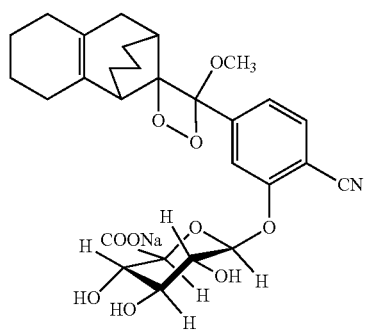

(149)

Example XXXIII

Synthesis of [(4-methoxy(D$_3$)-4-(3-acetoxy-4-chlorophenyl)]spiro[1,2-dioxetane-3,2'-adamantane]

This compound was synthesized by the following procedure.

Synthesis of [(3-acetoxy-4-chlorophenyl)-2-methoxy (D$_3$) methylene]adamantine Into a 250 mL three neck flask equipped with magnetic stirrer and pressure-equalizing addition funnel under a argon atmosphere charged solution of 2.34 parts of [(3-Hydroxy-4-chlorophenyl)-2-methoxy (D$_3$) methylene]adamantine and 1.7 parts of diisopropylethylamine in 50 mL of dichloromethane and cooled to 5° C. A solution of 0.65 parts of acetyl chloride in 10 mL of dichloromethane was added drop wise over 10 min to a cold solution and stirred for 25 mins. The mixture was stirred at room temperature for 26 hrs, diluted with 50 mL of dichloromethane and added deionized water 35 mL. The organic layer was separated, dried over anhydrous $Na_2SO_4$ and filtered. The solution was concentrated under reduced pressure and mixture was purified by column chromatography over silica gel with 10% ethyl acetate-hexanes to give 1.98 parts of the following compound confirmed by NMR.

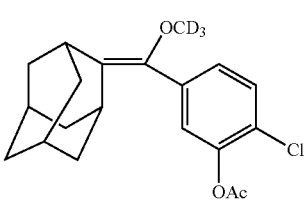

(150)

Synthesis of [(4-Methoxy(D$_3$)-4-(3-acetoxy-4-chlorophenyl)]spiro[1,2-dioxetane-3,2'-adamantane]

A solution of, 1.98 parts, [(3-acetoxy-4-chlorophenyl)-2-methoxy (D$_3$) methylene]adamantane in 75 mL of 1:1 mixture of dichloromethane-acetone was photo-oxidized as described above to give [(4-Methoxy(D$_3$)-4-(3-acetoxy-4-chlorophenyl)]spiro[1,2-dioxetane-3,2'-adamantane].

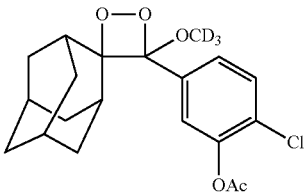

(151)

Example XXXIV

Synthesis of [(4-methoxy-4(3-acetoxy-4-cyanophenyl)]spiro[1,2-dioxetane-3-1,3-tricyclo[7.3.1.0$^{2,7}$]tridec-2,7-ene This compound was synthesized by the following procedure.

Synthesis of (3-Acetoxy-4-cyanophenyl)methoxymethylene tricyclo[7.3.1.0$^{2,7}$]tridec-2,7-ene Into a 250 mL three neck flask equipped with magnetic stirrer and pressure-equalizing addition funnel under argon atmosphere charged solution of 1.64 parts of 3-hydroxy-4-cyanophenyl)methoxymethylene tricyclo[7.3.1.0$^{2,7}$]tridec-2,7-ene and 1.03 parts of diisopropylethylamine in 40 mL of dichloromethane and cooled to 5° C. A solution of 0.45 parts of acetyl chloride in 5 mL of dichloromethane was added drop wise over 10 min and stirred for 30 mins. The mixture stirred at room temperature for 18 hr, diluted with 50 mL of dichloromethane and added 35 mL of deionized water. The organic layer was dried over anhydrous Na$_2$SO$_4$ and filtered. The solution was concentrated under reduced pressure and mixture was purified by column chromatography over silica gel with 10% ethyl acetate-hexanes to yield 1.39 parts of the following compound confirmed by NMR.

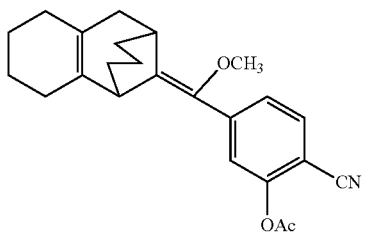
(152)

Synthesis of [(4-methoxy-4(3-acetoxy-4-cyanophenyl)]spiro[1,2-dioxetane-3-1,3-tricyclo[7.3.1.0$^{2,7}$] tridec-2,7-ene A solution of, 1.39 parts, (3-Acetoxy-4-cyanophenyl) methoxymethylene tricyclo[7.3.1.0$^{2,7}$]tridec-2,7-enein 50 mL of dichloromethane was photo-oxidized as described above to give of [(4-methoxy-4(3-acetoxy-4-cyanophenyl)] spiro[1,2-dioxetane-3-1,3-tricyclo[7.3.1.0$^{2,7}$]tridec-2,7-ene.

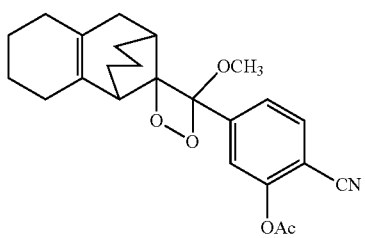
(153)

Example XXXV

Synthesis of [(4-methoxy(D$_3$)-4-(3-sulfate-4-chlorophenyl)]spiro[1,2-dioxetane-3,2'-adamantane]

This compound was synthesized by the following procedure.

Synthesis of [(3-sulfate-4-chlorophenyl)-2-methoxy (D$_3$)methylene]adamantane

Into a 250 mL three neck flask equipped with magnetic stirrer and pressure equalizing addition funnel under argon atmosphere charged solution of 3.7 parts of 3-hydroxy-4-cyanophenyl)methoxy(D$_3$)methylene tricyclo[7.3.1.0$^{2,7}$]tridec-2,7-ene and 2.96 parts of diisopropylethylamine in 40 mL of dichloromethane and cooled to 5° C. A solution of 1.52 parts of chlorosulfonic acid in 10 mL of dichloromethane was added drop wise over 10 min to a cold solution and was stirred for 30 min. The mixture was stirred at room temperature for 18 hrs, diluted with 50 mL of dichloromethane and added 25 mL of deionized water. The organic layer was separated, dried over anhydrous Na$_2$SO$_4$ and filtered. The solution was concentrated under reduced pressure and mixture was purified by column chromatography over silica gel eluting with 20% ethyl acetate-hexanes to yield 1.6 parts of the following compound confirmed by NMR.

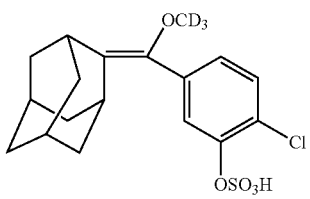
(154)

Synthesis of [(4-methoxy(D$_3$)-4-(3-sulfate-4-chlorophenyl)]spiro[1,2-dioxetane-3,2'-adamantane]

A solution of, 1.6 parts, [(3-sulfate-4-chlorophenyl)-2-methoxy(D$_3$)methylene]adamantanein 60 mL of dichloromethane was photo-oxidized as described above to give [(4-methoxy(D$_3$)-4-(3-sulfate-4-chlorophenyl)]spiro[1,2-dioxetane-3,2'-adamantane].

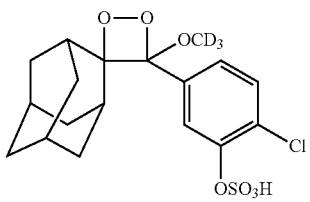
(155)

Example XXXVI

Synthesis of [(4-methoxy-4(3-sulfate-4-cyanophenyl)]spiro[1,2-dioxetane-3-1,3-tricyclo[7.3.1.0$^{2,7}$] tridec-2,7-ene This compound was synthesized by the following procedure.

Synthesis of (3-Sulfate-4-cyanophenyl)methoxymethylene tricyclo[7.3.1.0$^{2,7}$]tridec-2,7-ene Into a 250 mL three neck flask equipped with magnetic stirrer and pressure equalizing addition funnel under argon atmosphere charged solution of 1.64 parts of 3hydroxy-4-cyanophenyl)methoxymethylene tricyclo[7.3.1.0$^{2,7}$]tridec- 2,7-ene and 1.26 parts of diisopropylethylamine in 40 mL of dichloromethane and cooled to 5° C. A solution of 0.65 parts of chlorosulfonic acid in 5 mL of dichloromethane was added drop wise over 10 min to a cold solution and stirred for 30 mins. The mixture was stirred at room temperature for 18 hrs, diluted with 50 mL of dichloromethane and added 25 mL of deionized water. The organic layer was separated, dried over anhydrous Na₂SO₄ and filtered. The solution was concentrated under reduced pressure and crude mixture was purified by column chromatography over silica gel with 20% ethyl acetate-hexanes to yield 0.95 parts of the following compound confirmed by NMR.

(156)

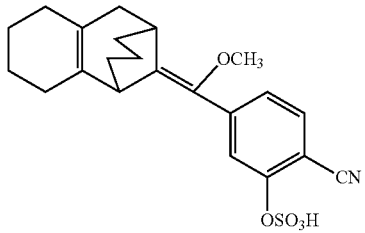

Synthesis of [(4-methoxy-4(3-sulfate-4-cyanophenyl)]spiro[1,2-dioxetane-3-1,3-tricyclo[7.3.1.0$^{2,7}$]tridec-2,7-ene A solution of, 0.95 parts, [(3-Sulfate-4-cyanophenyl) methoxymethylene tricyclo[7.3.1.0$^{2,7}$]tridec-2,7-enein 35 mL of dichloromethane was photo-oxidized as described above to give [(4-methoxy-4(3-sulfate-4-cyanophenyl)]spiro[1,2-dioxetane-3-1,3-tricyclo[7.3.1.0$^{2,7}$]tridec-2,7-ene of the following structure confirmed by NMR.

(157)

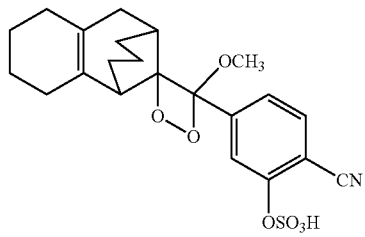

The invention claimed is:
1. A chemiluminescent assay formulation comprising:
at least one enzyme cleavable chemiluminescent compound which is a 1,2-dioxetane coupled acridane corresponding to the formula:

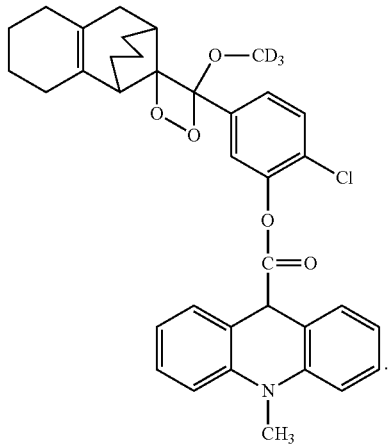 [SMILES: [2H]C([2H])([2H])OC1(c2ccc(Cl)c(OC(=O)C3c4ccccc4N(C)c4ccccc43)c2)OOC12C1CCCC2C2=C(CCCC2)C1]

\* \* \* \* \*